United States Patent
DiMaio et al.

(10) Patent No.: US 12,211,154 B2
(45) Date of Patent: Jan. 28, 2025

(54) SYSTEMS AND METHODS FOR REGION-BASED PRESENTATION OF AUGMENTED CONTENT

(71) Applicant: Intuitive Surgical Operations, Inc., Sunnyvale, CA (US)

(72) Inventors: Simon P. DiMaio, San Carlos, CA (US); Brandon D. Itkowitz, San Jose, CA (US); Terrence B. McKenna, III, San Francisco, CA (US); Govinda Payyavula, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 197 days.

(21) Appl. No.: 17/919,927

(22) PCT Filed: May 10, 2021

(86) PCT No.: PCT/US2021/031568
§ 371 (c)(1),
(2) Date: Oct. 19, 2022

(87) PCT Pub. No.: WO2021/231293
PCT Pub. Date: Nov. 18, 2021

(65) Prior Publication Data
US 2023/0186574 A1  Jun. 15, 2023

Related U.S. Application Data

(60) Provisional application No. 63/023,012, filed on May 11, 2020.

(51) Int. Cl.
*G06T 19/00* (2011.01)
*G06F 3/01* (2006.01)
(Continued)

(52) U.S. Cl.
CPC ............ *G06T 19/006* (2013.01); *G06F 3/013* (2013.01); *G06F 3/14* (2013.01); *G06T 19/20* (2013.01);
(Continued)

(58) Field of Classification Search
None
See application file for complete search history.

(56) References Cited

U.S. PATENT DOCUMENTS 7,239,330 B2  7/2007  Sauer et al.
7,774,044 B2  8/2010  Sauer et al.
(Continued)

FOREIGN PATENT DOCUMENTS

WO  WO-2016162789 A3  11/2016
WO  WO-2016207628 A1  12/2016
(Continued)

OTHER PUBLICATIONS

US 9,980,782 B1, 05/2018, Gibby (withdrawn)
(Continued)

*Primary Examiner* — Ryan M Gray

(57) ABSTRACT

A region-based augmentation system is configured to determine that a viewpoint of a user of a display device is directed within an anchor region of a physical world containing the user. In response, the system directs the display device to present augmented content in an evident manner. The evident manner comprises anchoring the augmented content relative to the viewpoint, such that the augmented content follows the viewpoint as the user moves the viewpoint within the anchor region. The system further determines that the viewpoint is directed outside of the anchor region by the user. In response, the system directs the display device to present the augmented content in a less evident manner. The presenting of the augmented content in the less evident
(Continued)

manner comprises presenting the augmented content less visibly than the evident manner and/or unanchoring the augmented content relative to the viewpoint. Corresponding methods and systems are also disclosed.

25 Claims, 11 Drawing Sheets

(51) Int. Cl.
  *G06F 3/14* (2006.01)
  *G06T 19/20* (2011.01)
  *G06V 10/25* (2022.01)
  *G06V 10/74* (2022.01)
  *G06V 20/40* (2022.01)

(52) U.S. Cl.
  CPC ............ *G06V 10/25* (2022.01); *G06V 10/761* (2022.01); *G06V 20/44* (2022.01); *G06T 2219/2016* (2013.01)

(56) References Cited

U.S. PATENT DOCUMENTS

| | | | |
|---|---|---|---|
| 9,645,785 B1 | 5/2017 | Hannaford et al. | |
| 9,681,925 B2 | 6/2017 | Azar et al. | |
| 9,789,608 B2 | 10/2017 | Itkowitz et al. | |
| 9,892,564 B1 | 2/2018 | Cvetko et al. | |
| 9,980,780 B2 | 5/2018 | Lang | |
| 10,068,378 B2 * | 9/2018 | Cabanier | G06T 19/006 |
| 10,653,495 B2 * | 5/2020 | Gregerson | G06T 15/20 |
| 10,838,210 B2 * | 11/2020 | Robaina | G06F 3/0304 |
| 2006/0189842 A1 | 8/2006 | Hoeg et al. | |
| 2006/0281971 A1 | 12/2006 | Sauer et al. | |
| 2013/0038707 A1 | 2/2013 | Cunningham et al. | |
| 2014/0275760 A1 | 9/2014 | Lee et al. | |
| 2015/0366628 A1 | 12/2015 | Ingmanson | |
| 2016/0049013 A1 * | 2/2016 | Tosas Bautista | G06F 3/012 |
| | | | 345/633 |
| 2016/0191887 A1 | 6/2016 | Casas | |
| 2016/0287337 A1 | 10/2016 | Aram et al. | |
| 2017/0056115 A1 | 3/2017 | Corndorf et al. | |
| 2017/0103583 A1 * | 4/2017 | Poulos | G06F 3/147 |
| 2017/0135775 A1 | 5/2017 | Cunningham et al. | |
| 2017/0172696 A1 | 6/2017 | Saget et al. | |
| 2018/0032130 A1 | 2/2018 | Meglan | |
| 2018/0116732 A1 | 5/2018 | Lin et al. | |
| 2018/0140362 A1 | 5/2018 | Caliet al. | |
| 2019/0018498 A1 * | 1/2019 | West | G06F 3/012 |
| 2019/0088162 A1 | 3/2019 | Meglan | |
| 2019/0183576 A1 | 6/2019 | Fahim et al. | |
| 2019/0231453 A1 | 8/2019 | Carnes et al. | |
| 2020/0054412 A1 | 2/2020 | Fuerst et al. | |
| 2020/0085511 A1 * | 3/2020 | Oezbek | A61B 90/39 |

FOREIGN PATENT DOCUMENTS

| | | |
|---|---|---|
| WO | WO-2017151752 A1 | 9/2017 |
| WO | WO-2018032083 A1 | 2/2018 |
| WO | WO-2018052966 A1 | 3/2018 |
| WO | WO-2018118411 A1 | 6/2018 |
| WO | WO-2019177711 A1 | 9/2019 |

OTHER PUBLICATIONS

International Preliminary Report on Patentability for Application No. PCT/US2021/031568 mailed Nov. 24, 2022, 11 pages.
International Search Report and Written Opinion for Application No. PCT/US2021/031568, mailed Aug. 11, 2021, 15 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

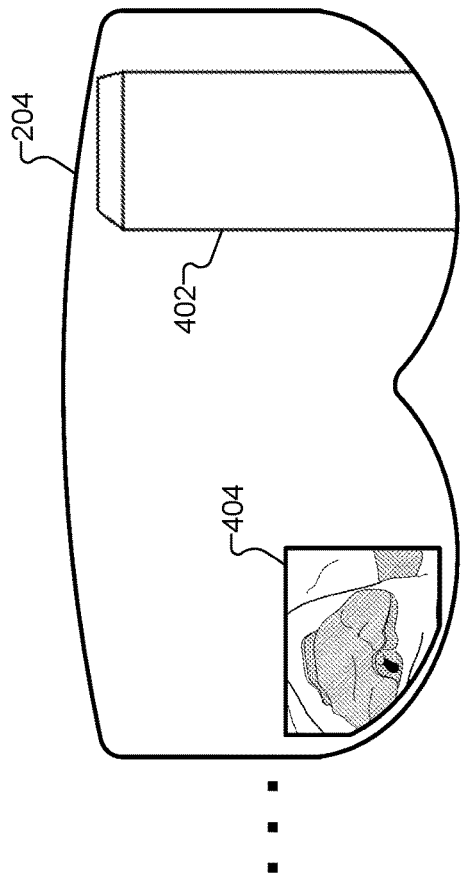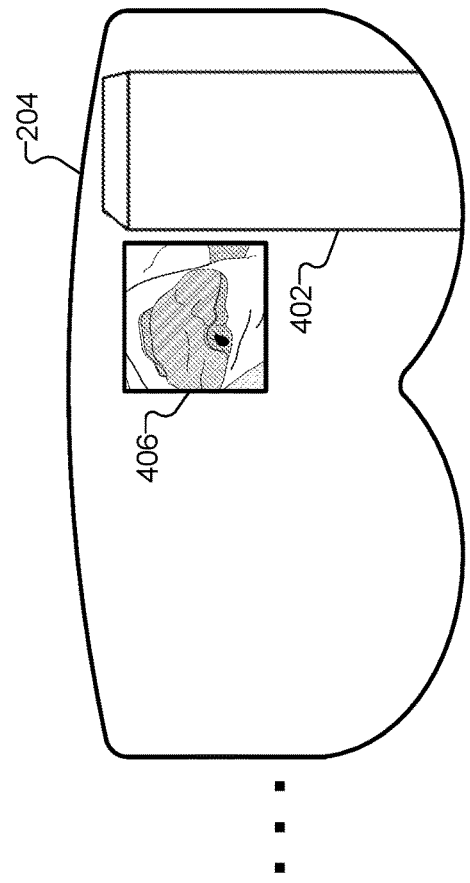
Fig. 4A
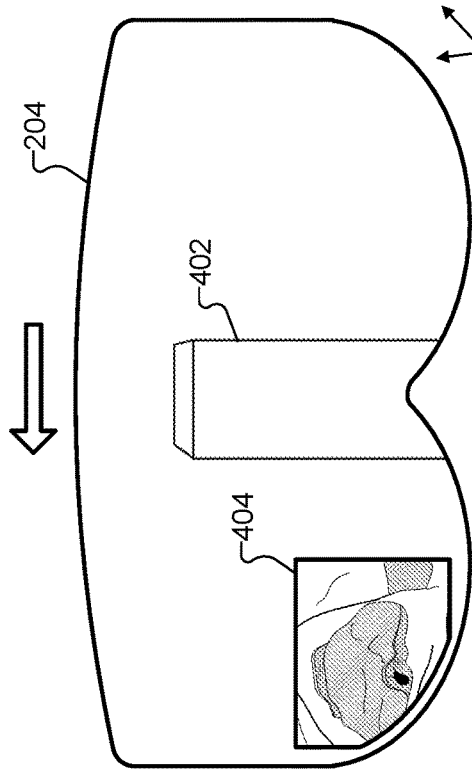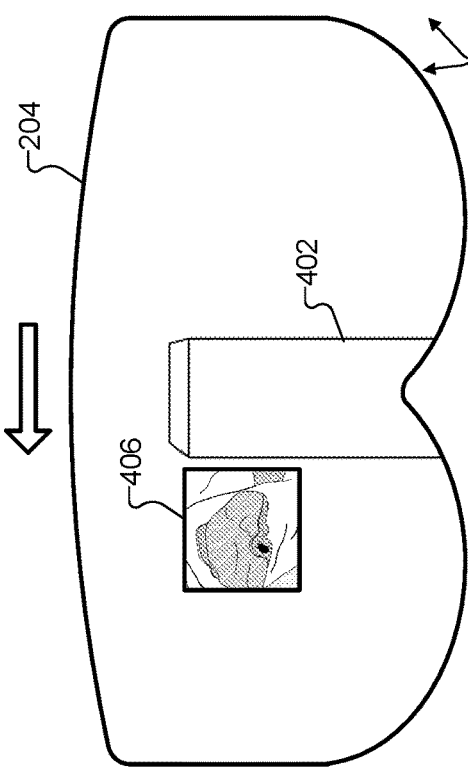
Fig. 4B

SYSTEMS AND METHODS FOR REGION-BASED PRESENTATION OF AUGMENTED CONTENT

RELATED APPLICATIONS

The present application is a U.S. National Stage Application under 35 U.S.C. § 371 of International Application No. PCT/US2021/031568, filed on May 10, 2021, which claims priority to U.S. Provisional Patent Application No. 63/023,012, filed May 11, 2020, the contents of which are hereby incorporated by reference in their entirety.

BACKGROUND INFORMATION

Mixed reality technologies allow a user to view a world that incorporates both real elements (i.e., real elements that actually surround the user in the real world) and virtual elements (i.e., synthetic elements that are presented for viewing by the user but that are in fact not present in the real world). For example, augmented reality technologies, certain virtual reality technologies and other forms of extended reality may all be considered mixed reality technologies as that term is used herein.

Various applications and use cases may be served by using mixed reality technology to present augmented content (i.e., one or more virtual elements) onto a view of the real world. However, it may not be the case that a prominent display of such augmented content is equally desirable at all times or for every situation.

SUMMARY

Systems and methods for region-based presentation of augmented content to a user are described herein. For instance, one embodiment of such a region-based augmentation system includes a memory storing instructions and a processor communicatively coupled to the memory and configured to execute the instructions to perform certain operations. For example, the operations may include determining that a viewpoint of a user of a display device is directed within an anchor region of a physical world containing the user. The operations may also include directing, in response to the determination that the viewpoint is directed within the anchor region, the display device to present augmented content in an evident manner. For example, the evident manner may include anchoring the augmented content relative to the viewpoint, such that the augmented content follows the viewpoint as the user moves the viewpoint within the anchor region. The operations may further include determining that the viewpoint is directed outside of the anchor region by the user, and, in response to the determination that the viewpoint is directed outside of the anchor region, directing the display device to present the augmented content in a less evident manner. For example, presenting the augmented content in the less evident manner may include presenting the augmented content less visibly than the evident manner or unanchoring the augmented content relative to the viewpoint.

An example embodiment of a region-based augmentation method may be performed by a region-based augmentation system. For example, the method may include determining that a viewpoint of a user of a display device is directed within an anchor region of a physical world containing the user. The method may also include directing, in response to the determination that the viewpoint is directed within the anchor region, the display device to present augmented content in an evident manner. For example, the evident manner may include anchoring the augmented content relative to the viewpoint, such that the augmented content follows the viewpoint as the user moves the viewpoint within the anchor region. The method may further include determining that the viewpoint is directed outside of the anchor region by the user, and, in response to the determination that the viewpoint is directed outside of the anchor region, directing the display device to present the augmented content in a less evident manner. For example, presenting the augmented content in the less evident manner may include presenting the augmented content less visibly than the evident manner or unanchoring the augmented content relative to the viewpoint.

Various other example embodiments may be implemented by a non-transitory, computer-readable medium storing instructions that, when executed, direct a processor of a computing device to perform any of the operations described herein.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 4A shows illustrative augmented content that is anchored relative to a viewpoint of a user of a display device according to principles described herein.

FIG. 4B shows illustrative augmented content that is anchored relative to the physical world according to principles described herein.

DETAILED DESCRIPTION

Figure 1:
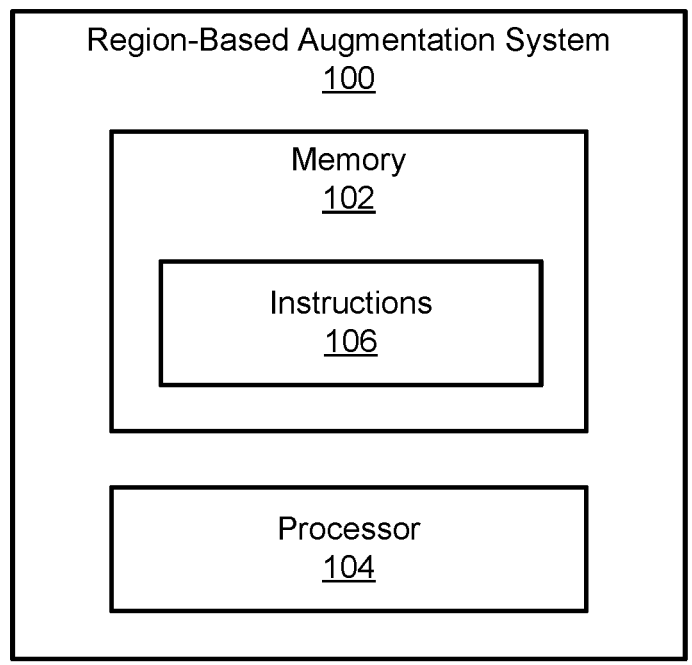
FIG. 1 shows an illustrative region-based augmentation system for region-based presentation of augmented content in an evident manner to a user according to principles described herein.

Systems and methods for region-based presentation of augmented content in an evident manner to a user are described herein. As used herein, "region-based" presentation of augmented content refers to a presentation of augmented content to a viewer (e.g., a viewer experiencing mixed reality), where that presentation accounts for a region of the world that is being viewed. For example, as will be described in more detail herein, the viewer's view of the world may be augmented with content presented in an evident manner (e.g., anchored relative to a viewpoint of the viewer, presented at a particular size, presented with minimal or no transparency, etc.) when the view is directed in one region of the world, while the augmented content may be presented in a less evident manner (e.g., unanchored from the viewpoint of the viewer, presented at a smaller size, presented with a greater degree of transparency, not presented at all, etc.) when the view is not directed in that one region of the world. As used herein, a region of the physical world where it is generally desirable for augmented content to be presented in the evident manner is referred to herein as an anchor region.

Systems and methods described herein for region-based presentation of augmented content may provide useful benefits and advantages in a wide variety of circumstances and use cases. For example, various applications facilitated by extended reality technologies such as recreational or entertainment applications (e.g., video games, television or movie content, exercise programs, etc.), industrial applications (e.g., manufacturing, robotic, and other applications), educational and training applications, consumer and professional applications, communication applications, and so forth may all be served by implementations of region-based augmentation systems and methods described herein.

Aspects of this disclosure are described in reference to computer-assisted systems and devices, which may include systems and devices that are manually manipulated, remote-controlled, semi-autonomous, autonomous, etc.; and including systems and devices that are robotic or non-robotic, teleoperated or non-teleoperated, etc. Further, aspects of this disclosure are described in terms of an implementation using a surgical system, such as the da Vinci® Surgical System commercialized by Intuitive Surgical, Inc, of Sunnyvale, California. However, inventive aspects disclosed herein may be embodied and implemented in various other ways. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

Thus, the principles described herein have broad applicability to many types of applications and use cases. The following description will often present a particular type of use case for convenience of description. Specifically, region-based augmentation systems and methods described below will often be described and illustrated in a medical context that will be understood to relate to various surgical and non-surgical medical procedures and/or operations (e.g., diagnostic procedures, treatment procedures, training procedures, etc.) for which medical personnel may utilize mixed reality technologies such as, for example, one that involves an augmented reality display device. While such medical contexts are used as examples, it will be appreciated that the principles described herein may find significant applicability to various other types of contexts, scenarios, and applications.

To illustrate a particular medical example, a minimally-invasive surgical procedure performed using a computer assisted (e.g., robotically-controlled) medical system will be considered (a specific example of such a system will be described and illustrated in more detail below in relation to FIG. 10). Surgical staff performing intracorporeal tasks at the bedside of such a procedure have conventionally visualized surgical endoscope video and/or other imagery using physical monitors mounted to walls or ceilings of the operating rooms, or to equipment in the operating rooms. The placement of monitors in these types of locations may be non-ergonomic and inconvenient, and may make it difficult for the staff members to visualize intracorporeal events and to efficiently perform their assigned tasks during the procedure.

Systems and methods described herein may provide significant benefits in this type of medical context, such as by presenting augmented content (e.g. additional imagery, video, etc.) to the medical staff members' eyes during the procedure in an evident manner when the content is determined to be desirable, useful, or convenient. Systems and methods described herein can also make less evident the augmented content when the content is determined not to be desirable, useful, or convenient. Many of these benefits will be described and/or made apparent in the description below. Various embodiments will now be described in more detail with reference to the figures.

FIG. 1 shows an illustrative region-based augmentation system 100 ("system 100") for region-based presentation of augmented content (e.g., for a medical example, for use by a medical staff member assisting or performing a medical procedure, etc.). As shown, system 100 may include, without limitation, a memory 102 and a processor 104 selectively and communicatively coupled to one another. It will be understood that memory 102 may represent one or more memory modules of the same or different types (e.g., transient memory, non-transient storage, etc.). Similarly, processor 104 may represent one or more processing units of the same or different types (e.g., central processing units ("CPUs"), graphics processing units ("CPUs"), embedded devices, customizable devices such as field programmable gate arrays ("FPGAs"), etc.).

In some examples, memory 102 and processor 104 may be integrated into a single device, while, in other examples, either or both of memory 102 and processor 104 may be distributed between multiple devices and/or multiple locations. For instance, in one implementation of system 100, a display device associated with a particular user may include one or more built-in processing units, memory modules, sensors, communication interfaces, and so forth, all of which may interoperate to implement system 100. In contrast, in other implementations of system 100, some or all of these components may not be integrated into the display device itself but, rather, may be implemented on other computing systems as may serve a particular implementation (e.g., edge servers, cloud servers, computing devices integrated with other components of a computer-assisted medical system such as will be described in relation to FIG. 10 below, etc.).

Memory 102 may store or otherwise maintain executable data used by processor 104 to perform any of the functionality described herein. For example, memory 102 may store instructions 106 that may be executed by processor 104 to perform any of the functionality described herein. Instructions 106 may be implemented by any suitable application, software, code, and/or other executable data instance. Memory 102 may also maintain any data received, generated, managed, used, and/or transmitted by processor 104.

Processor 104 may be configured to perform, such as by being configured to execute instructions 106 stored in memory 102 to perform, various processing functions associated with region-based presenting of augmented content. For example, processor 104 may determine that a viewpoint of a user of a display device is directed within an anchor region of a physical world containing the user, and may direct, in response to the determination that the viewpoint is directed within the anchor region, the display device to present augmented content in an evident manner.

Referring to a medical procedure context example, the display device may be implemented as a head-mounted augmented reality display that the user utilizes to perform or help with a medical procedure that is being performed on a body within a medical area. Processor 104 may define the anchor region based on regions entered by the user. Processor 104 may also define the anchor region semi-automatically, such as by presenting for selection the anchor region based on operating conditions or other factors. Processor 104 may also define the anchor region automatically, such as by identifying the anchor region by itself, based on various parameters detected or received. Example operating conditions and other factors include: a location, size, or other geometric feature of a site for the medical procedure, a system to be used in the procedure, a tool for performing the procedure, the user or some other person associated with the procedure, a type of the procedure or system or tool, stored user preference information, etc. Also, the augmented content may be configured to assist the user in performing the medical procedure. For instance, the augmented content may comprise textual information, graphical information (e.g., video, photographs, sensor images, symbols, drawings, graphs, etc.), or both textual and graphical information. As a specific example of graphical information, the augmented content may feature one or more external or internal views of the body receiving the medical procedure, Such views may be captured preoperatively or intraoperatively, and may be captured by any appropriate imaging device. Example imaging devices include: a camera for capturing visible light or non-visible light, an endoscope, an ultrasound module, a florescence imaging module, a fluoroscopic imaging module, etc. In certain examples, the augmented content may depict a model that has been generated based on preoperative data or that is generated and/or updated based on intraoperative data.

In another medical procedure example, the user may be a person helping to perform the medical procedure and the anchor region may be associated with the body receiving the medical procedure. For example, the anchor region may comprise a space proximate to a portion of the body or the entire body, a space that surrounds the portion of the body or the entire body, etc.

Examples of such medical procedures include surgical procedures as well as non-surgical procedures. Examples of such medical procedures include those for diagnostics, treatment and therapy, cosmetics, imaging, data gathering, training, and demonstration. Medical procedures may or may not utilize minimally invasive techniques involving a computer-assisted medical system. Examples of bodies on which medical procedures may be performed include live human patients or other suitable bodies that may be living or non-living, biological or non-biological, natural or artificial, and so forth. For example, bodies of animals, human cadavers, animal cadavers, portions of human or animal anatomy, tissue removed from human or animal anatomies (which may or may not be re-implanted within the human or animal anatomy), non-tissue work pieces, training models, and so forth, may all be examples of bodies on which medical procedures may be performed.

When processor 104 directs the display device to present the augmented content in the evident manner, processor 104 may, in certain implementations, anchor the augmented content relative to the viewpoint of the user such that the augmented content follows the viewpoint as the user moves the viewpoint within the anchor region. In this way, the augmented content may remain easily viewable to the user while he or she is looking within the anchor region (e.g., looking in the direction of the anchor region), and the ergonomic and efficiency are improved. As will be described below, there may also be situations where this anchoring of the augmented content to the viewpoint is changed or is performed in other ways.

While the user continues to direct his or her viewpoint within the anchor region, system 100 may continuously present the augmented content in the evident manner, where the evident manner includes anchoring the augmented content relative to the viewpoint. However, if the user directs the viewpoint to another part of the physical world away from the anchor region, system 100 may automatically transition to presenting the augmented content in a less evident manner. Presenting in a less evident manner may be helpful to reduce visual distractions, increase convenience, comfort, efficiency, or the like where the user is performing a task not aided by an evident presentation of the augmented content. Presenting in a less evident manner may comprise presenting the augmented content less visibly than the evident manner, or unanchoring the augmented content relative to the viewpoint. Presenting content less visibly than the evident manner may, in some examples, include not presenting the augmented content at all.

To this end, processor 104 may determine that the viewpoint is directed outside of the anchor region by the user, and, in response to the determination that the viewpoint is directed outside of the anchor region, processor 104 may direct the display device to present the augmented content in the less evident manner. For example, processor 104 may present the augmented content in the less evident manner by presenting the augmented content less visibly than the evident manner, such as by presenting the augmented content with a smaller size or with higher transparency, by ceasing to display the augmented content, or the like. As another example, processor 104 may present the augmented content in the less evident manner by unanchoring the augmented content relative to the viewpoint; in some instances, processor 104 may instead anchor the augmented content to the physical world.

In some implementations, system 100 (e.g., processor 104) may be configured to perform region-based presenting of augmented content in an evident manner to a user in real time. As used herein, a function may be said to be performed in real time when the function relates to or is based on dynamic, time-sensitive information and the function is performed while the time-sensitive information remains accurate or otherwise relevant. Due to processing times, communication latency, and other inherent delays in physical systems, certain functions may be considered to be performed in real time when performed immediately and without undue delay, even if performed after a small delay (e.g., a delay up to a few seconds or the like). As one example of real-time functionality, processor 104 may direct the display device to present augmented content in an evident manner, a less evident manner, or to switch between (or begin transitioning between) these different manners of presentation in a manner that is responsive to the user's movement of the display device.

Figure 2:
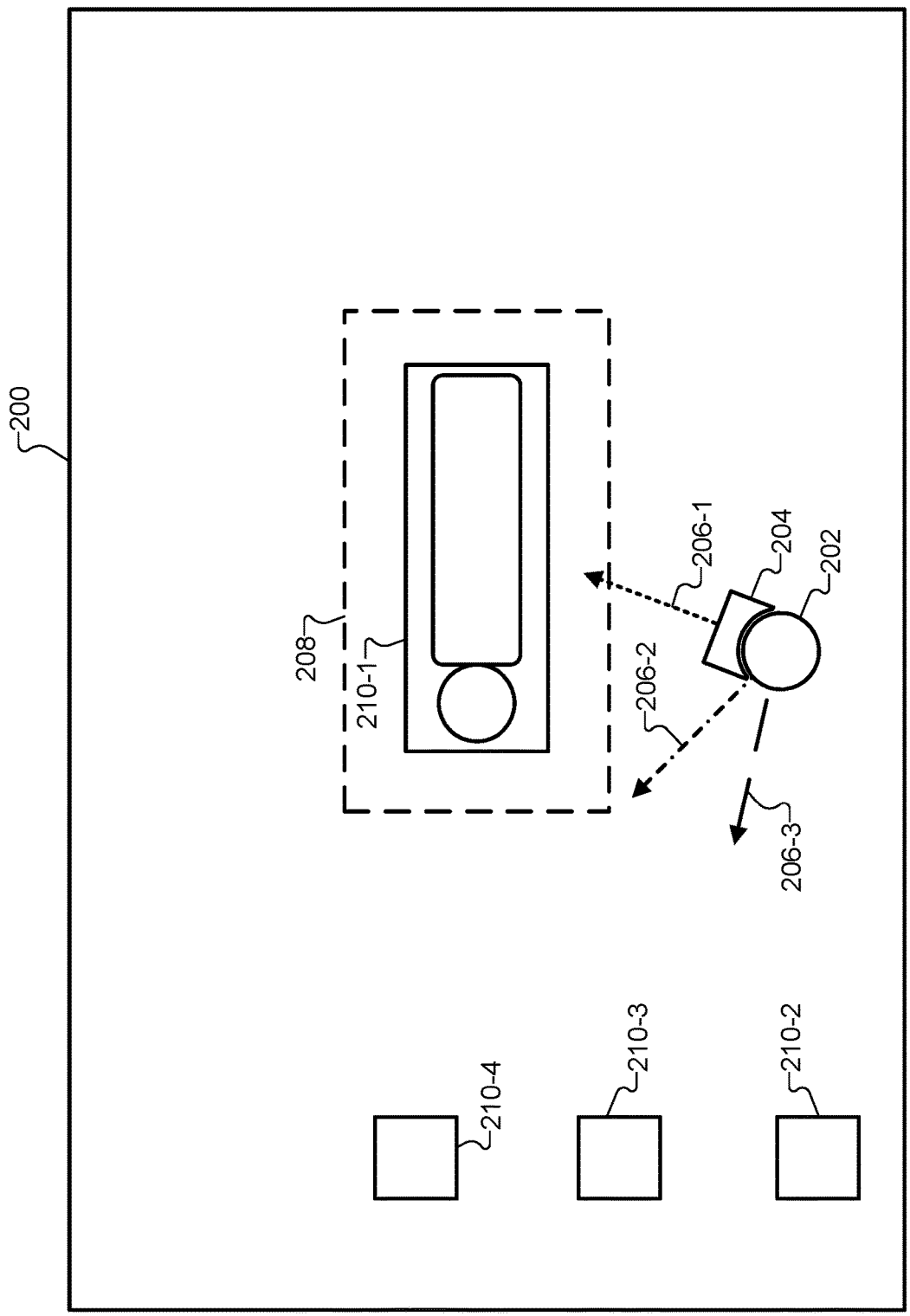
FIG. 2 shows certain aspects of an illustrative implementation of the region-based augmentation system of FIG. 1 in operation according to principles described herein.

FIG. 2 shows certain aspects of an illustrative implementation of system 100 in operation, Specifically, as shown, FIG. 2 depicts a top view of a physical world 200, a user 202 contained within physical world 200, and a display device 204 being used by user 202. The physical world 200 is the real world that contains user 202. A viewpoint 206 of user 202 may be an actual or estimated direction and/or location of viewing focus for user 202, or may be determined based on the direction and/or location of the viewing focus. In various implementations, viewpoint 206 is determined based on a gaze direction or gaze location of user 202, based on a direction or location that the head of user 202 is directed, based on a direction or location that one or more eyes of user 202 are determined to be engaged, or based on a field of view associated with display device 204. Viewpoint 206 may be freely movable by user 202 to be directed, at different times, toward or at any of various areas of physical world 200. Three illustrative viewpoints 206 (labeled as viewpoints 206-1 through 206-3) are depicted in FIG. 2 using different styles of lines that originate from user 202 and move outward in particular directions. The top view of FIG. 2 further depicts an anchor region 208 and a plurality of objects 210 (e.g., objects 210-1 through 210-4) included within physical world 200. Each of these elements depicted in FIG. 2 will now be described in more detail.

FIG. 2 depicts a rectangular portion of physical world 200, and will be understood to represent a portion of the world such as a room or another suitable area that includes at least one anchor region and where system 100 may perform region-based presentation of augmented content according to principles described herein. In a medical procedure context such as has been described, for instance, physical world 200 may represent an operating room or other medical area where a medical procedure is being performed.

User 202 may represent any user of display device 204. In a medical example, user 202 may be a person working to perform or assist a medical procedure, such as a nurse, an assistant, a clinician, a surgeon, a proctor, a trainee for any of these roles, etc.

Display device 204 may be implemented by any suitable device that is configured to be used by user 202 to present augmented content based on a region of physical world 200 to which user 202 directs viewpoint 206. In some examples, display device 204 may be implemented by a head-mounted display device configured to present augmented content in a field of view of a wearer of the device as the wearer moves the viewpoint within physical world 200 using head motions. In various implementations, head-mounted display devices may be implemented by dedicated augmented reality devices, by general purpose mobile devices (e.g., tablet computers, smartphones, etc.) that are worn in front of the eyes using a head-mounting apparatus, or by other types of display devices.

In certain examples, display device 204 may be implemented by devices that are not worn on the head. For instance, display device 204 may be implemented by a handheld device (e.g., a mobile device such as a smartphone, tablet, etc.) that may be pointed in different directions and/or focused to different distances within physical world 200, by a projection-based augmented reality device that may project augmented content onto physical surfaces in physical world 200, or by other non-head-mounted devices that are capable of presenting augmented reality content in various other suitable ways. In certain such implementations, viewpoint 206 of user 202 may be determined as a direction and/or location of view of display device 204, instead of a direction and/or location of view of user 202.

In some implementations, display device 204 may include a camera that captures a view of physical world 200 and passes the view in real-time through to a display screen viewable by the user, to present the view of physical world 200 to user 202. Certain general-purpose mobile devices used to implement display device 204 may operate in this manner, for example. In other types of implementations, display device 204 may include a see-through screen that allows light to pass through from physical world 200 to reach the eyes of user 202, and that allows augmented content to be presented on the screen by being overlaid onto the view of the physical world viewable through the screen. When such an approach is taken by a head-mounted display device and the head-mounted display device is worn by user 202, such as via augmented reality glasses, the see-through screen may be positioned in front of the eyes of user 202. As such, the see-through screen may allow user 202 to direct viewpoint 206 at will, and augmented content may be presented to allow user 202 to see physical world 200 together with the augmented content by way of the see-through screen.

In various instances, display device 204 may further include computer hardware and software (e.g., a processor, a memory storing instructions, etc.) sufficient to implement system 100, or to communicate with another computing system that fully or partially implements system 100.

In some examples, system 100 determines viewpoint 206 based on at least a viewing direction defined based on the location and orientation of display device 204, such as illustrated in viewpoints 206-1 through 206-3 in FIG. 2. In some examples, system 100 determines viewpoint 206 based on at least a viewing direction defined based on the location and orientation of user 202, such as based on the orientation of a head of user 202. In yet another example, system 100 may determine the direction of viewpoint 206 based on additional or other parameters. For example, system 100 may determine the direction of viewpoint 206 based on at least a gaze direction of the eyes of user 202. Accordingly, in such implementations, system 100 may employ eye tracking technology to determine viewpoint 206. In these examples where system 100 determines viewpoint 206 based on a viewing direction, system 100 may determine that the viewpoint is directed within an anchor region (e.g. anchor region 208) by determining that the viewing direction intersects with the anchor region.

In some examples, system 100 determines viewpoint 206 as a location of visual focus. In such examples, viewpoint 206 may be described by a viewing direction and a viewing distance from display 204 or user 202, For example, the system 100 may determine viewpoint 206 based on a viewing direction and a focal distance of the eyes of user 202. In such examples, system 100 may determine that the viewpoint is directed within an anchor region (e.g. anchor region 208) by determining that the viewing direction and distance falls within the anchor region.

In the example illustrated in FIG. 2, user 202 is shown to be directing viewpoint 206 toward object 210-1 and within anchor region 208. It will be understood, however, that at subsequent points in time (as will be described below), user 202 may direct viewpoint 206 in other directions, such as the directions illustrated by viewpoints 206-2 and 206-3, by turning his or her head and/or eyes to look elsewhere, or by moving display device 204.

Objects 210 may each represent any object or other imagery that may be present in physical world 200. For instance, in the example where physical world 200 includes a medical area (e.g., an operating room, etc.) where a medical procedure is being performed, object 210-1 may represent an operating table upon which a body rests while the medical procedure is performed. Objects 210-2 through 210-4 may then be other types of objects present in the medical area, such as other personnel, medical equipment (e.g., components of a computer-assisted medical system, a table upon which instruments are held, etc.), or other objects as may serve a particular implementation.

As shown in FIG. 2, and as will be described in more detail below, anchor region 208 may be defined within physical world 200 as an area associated with object 210-1. In this example, as illustrated, anchor region 208 may be defined to enclose the entire operating table and body being operated on, as well as a small amount of space surrounding the operating table and body.

As has been described, system 100 may be configured to determine when viewpoint 206 is directed within or outside of an anchor region. System 100 may perform this determination in any suitable way, such as by using an appropriate sensor of display device 204 (e.g., an image sensor, an accelerometer, a gyroscopic sensor, a magnetometer, etc.), by using external tracking sensors (e.g., optical tracking sensors mounted in physical world 200 and configured to monitor user 202 and/or display device 204, optical or motion sensors mounted to user 202 or display device 204, etc.), and/or based on any suitable tracking techniques or algorithms (e.g., registration or spatial tracking techniques, simultaneous localization and mapping ("SLAM") algorithms, etc.) to determine viewpoint 206. For example, such sensors and/or techniques can be used to determine the location of display device 204 or user 202, how display device 204 or user 202 is oriented in space, etc., to determine how viewpoint 206 is directed. Where viewpoint 206 is based on a viewing direction, system 100 may determine that viewpoint 206 is directed within anchor region 208 when viewpoint 206 intersects with anchor region 208; in this example, when viewpoint 206 is determined not to intersect with anchor region 208, system 100 then determines that viewpoint 206 is not directed within, and is directed outside of, anchor region 208. Where viewpoint 206 is based on a viewing location, system 100 may determine that viewpoint 206 is directed within anchor region 208 when the viewing direction and viewing distance falls within anchor region 208; in this example, when the viewing direction and viewing distance is determined to place viewpoint 206 outside of the anchor region 208, system 100 then determines that viewpoint 206 is not directed within, and is directed outside of, anchor region 208.

As shown in FIG. 2, and as may be determined by system 100 in any of these ways, viewpoint 206-1 is directed by user 202 within anchor region 208, viewpoint 206-2 is directed toward a boundary of anchor region 208, and viewpoint 206-3 is directed outside of anchor region 208. Fields of view associated with each of these viewpoints 206 will now be illustrated and described in more detail in relation to FIGS. 3-8.

Figure 3:
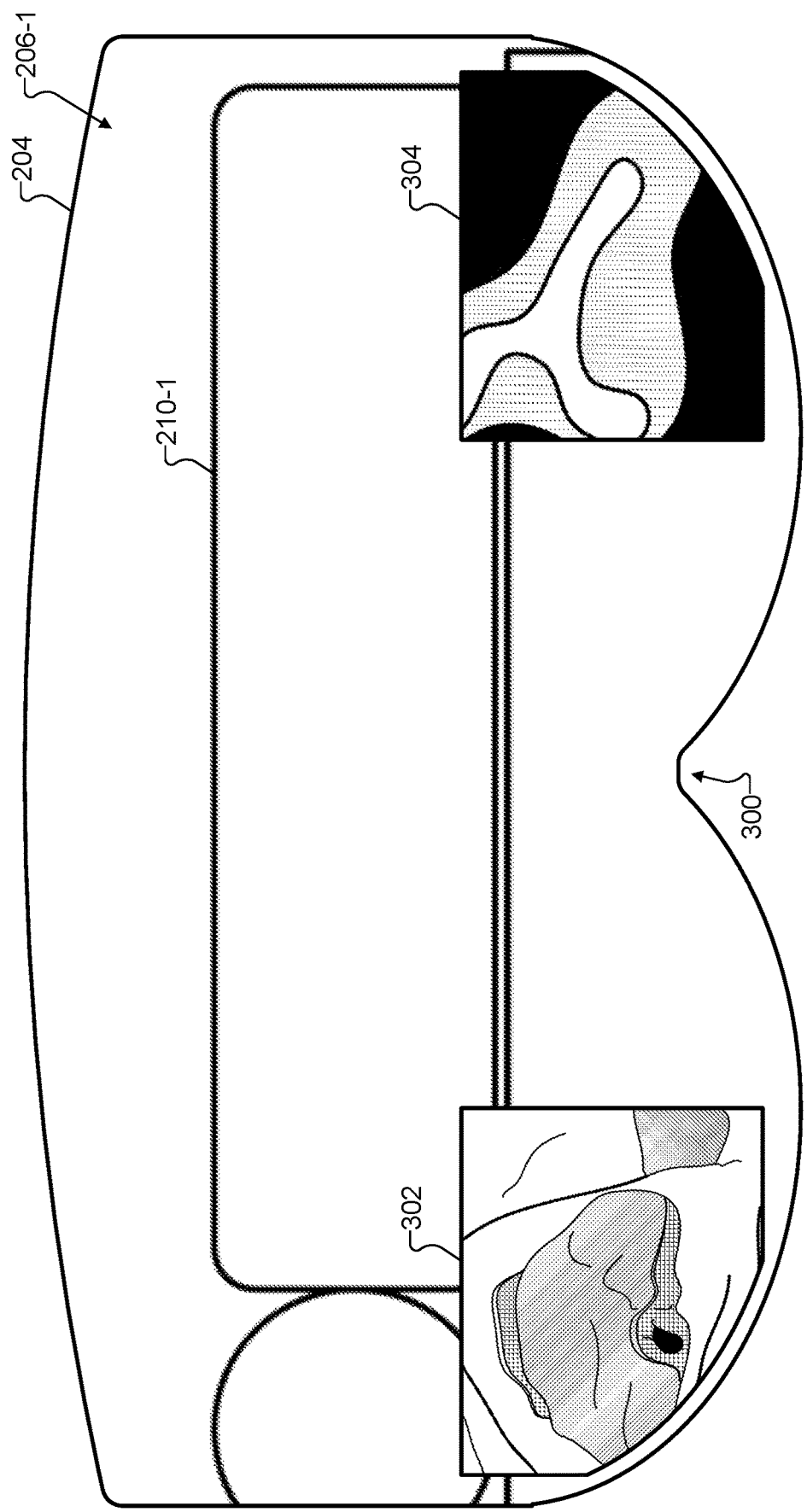
FIG. 3 shows an illustrative presentation of augmented content in an evident manner for when a viewpoint of a user is directed within an anchor region of the physical world according to principles described herein.

FIG. 3 shows an illustrative field of view associated with viewpoint 206-1, which is directed within anchor region 208. As shown, viewpoint 206-1 is illustrated as a perspective view, from a vantage point of user 202, of a portion of object 210-1 that is viewable through or on display device 204. In FIG. 3 and subsequent illustrations herein, display device 204 is shaped roughly like a viewport of an illustrative head-mounted display device or pair of glasses, including a large viewable space with a notch 300 where the device could rest on the nose. This shape is used for illustrative convenience only, and it will be understood that various implementations may employ various types and shapes of viewports, including rectangular viewports. Further, display device 204 may be configured to present monoscopic views, stereoscopic views, 3-D views, and so forth.

As user 202 views object 210-1 and/or other objects and imagery in physical world 200, FIG. 3 shows that display device 204 may present augmented content that is not actually present at the scene but is superimposed so as to be viewable by user 202 together with the imagery and objects that are present in physical world 200. More particularly, FIG. 3 shows an illustrative presentation of augmented content in an evident manner within the field of view associated with viewpoint 206-1. For example, as shown, augmented content 302 is of a first type (e.g.; showing real-time imagery, such as an internal view of the body currently being captured by an imaging instrument such as an endoscope inserted within the body, an ultrasonic probe, a fluoroscopic device, etc.). Augmented content 302 is shown to be displayed at a location in the bottom-left portion of the field of view in FIG. 3, while augmented content 304 is of a second type (e.g., showing a non-real-time imagery, such as preoperative images such as those captured by MRI or CT scans, an anatomical model generated based on preoperative imaging, etc.). Augmented content 302 and 304 may be related to each other, such as by providing complementary information, or by changing with each other. As a specific example, in some instances, augmented content 302 may comprise a real-time image of the anatomy captured by an imaging device, and augmented content 304 may comprise a model or preoperative image of the same anatomy registered directly or indirectly to the real-time image; in this example, as the augmented content 302 is updated to show a different part of the anatomy, augmented content 304 is automatically updated to depict the same different part, or vice versa. Augmented content 304 is shown to be displayed at a location in the bottom-right portion of the field of view in FIG. 3. At the time period represented in FIG. 3 (i.e., when viewpoint 206 is directed within anchor region 208 as shown for viewpoint 206-1), one or both of augmented contents 302 and 304 may be presented in an evident manner. As shown, presenting augmented content in the evident manner in accordance with the example of FIG. 3 includes anchoring the augmented content relative to viewpoint 206 such that the augmented content follows viewpoint 206 as user 202 moves viewpoint 206 within anchor region 208.

The augmented content shown to be presented by display device 204 in FIG. 3 includes two virtual screens in particular locations (i.e., augmented content 302 comprising a first virtual screen and 304 comprising a second virtual screen). However, it will be understood that the augmented content in a particular implementation can comprise any type, number, and locations of elements, with each element having any suitable form or shape appropriate for the implementation. For example, in certain instances, the augmented content may comprise graphical or textual displays not in the form of virtual screens. As another example, in certain instances, the augmented content may comprise fewer or more virtual screens. In some examples, multiple augmented contents may be aligned horizontally or vertically. In some examples, different inputs to system 100, or motions of display device 204 (e.g., the user pitching display device up and down, yawing motions side to side, etc.) may be interpreted by system 100 as indications to direct display device 204 to present, anchor, and/or otherwise manipulate the augmented content in particular ways.

Augmented content may be configured to present any information in any manner as may serve a particular implementation. For instance, as shown in the medical procedure example of FIG. 3, augmented content 302 is implemented as comprising a virtual screen that presents one type of internal view of the body of object 210-1, while augmented content 304 is implemented as comprising a virtual screen separate from that of augmented content 302, and that presents a different type of internal view of the body of object 210-1. It will be understood that the examples of augmented content shown in augmented content 302 and 304 are for illustration purposes only, and that various types of other augmented content may be presented in other medical procedure examples or other non-medical examples.

Each of augmented contents 302 and 304 may be anchored to viewpoint 206, anchored to physical world 200, anchored to some other reference, or not anchored, in any suitable way. For instance, the augmented content presented by display device 204 may include first augmented content (e.g. a first virtual screen such as that shown in FIG. 3 for augmented content 302) anchored to viewpoint 206 (e.g., at the bottom-left portion of the field of view) and second augmented content (e.g. a second virtual screen such as that shown in FIG. 3 for augmented content 304) anchored to viewpoint 206 at a different location (e.g., at the bottom-right portion of the field of view). As another example, the augmented content presented by display device 204 may include first augmented content (e.g. a first virtual screen such as that shown in FIG. 3 for augmented content 302) anchored to viewpoint 206 and second augmented content (e.g. a second virtual screen such as that shown in FIG. 3 for augmented content 304) anchored at a fixed location relative to physical world 200 (e.g., to a location referenced to object 210-1).

Accordingly, as user 202 directs viewpoint 206 to different areas of physical world 200, augmented content such as augmented contents 302 and 304 may be anchored to or unanchored from viewpoint 206, or be anchored or unanchored from physical world 200. FIGS. 4A and 4B illustrate the difference between anchoring an augmented content relative to a viewpoint (in a fixed location relative to the viewpoint or aspect of the viewpoint) and anchoring an augmented content relative to the physical world (in a location fixed relative to the physical world or aspect of the physical world, such as to coordinates defined in the physical world, to a real object in the physical world, etc.). FIG. 4A shows a viewpoint anchor mode 400-1 in which illustrative augmented content is anchored relative to a viewpoint of a user of display device 204, while FIG. 4B shows a physical-world anchor mode 400-2 in which illustrative augmented content is anchored relative to the physical world as viewed by the user by way of display device 204. Each of FIGS. 4A and 4B shows the view at an initial time (on the left sides of FIGS. 4A and 4B) and at a subsequent time after display device 204 has been moved to the left (in accordance with a movement arrow displayed above the initial view) and the viewpoint has been redirected to a different position, as shown on the right sides of FIGS. 4A and 4B. In each of these depictions of the field of view visible on or through display device 204, an object 402 in the physical world is depicted (e.g., object 402 can be one of objects 210 in physical world 200). Object 402 can be viewed when user 202 directs the view associated with display device 204 accordingly. FIG. 4A shows a viewpoint-anchored augmented content 404 that is anchored relative to the viewpoint (in this example, fixed in a location relative to the viewpoint). FIG. 4B shows a physical-world-anchored augmented content 406 that is anchored to the physical world (in this particular example, fixed in a location relative to object 402).

As illustrated in FIG. 4A, when the user redirects display device 204 a few degrees to the left and a little closer to object 402 (as evidenced by object 402 shifting to the right and getting slightly bigger within the field of view from the initial time to the subsequent time), viewpoint-anchored augmented content 404 remains in the same place relative to the viewpoint. More particularly, as shown in FIG. 4A, viewpoint-anchored augmented content 404 remains the same size and remains at the fixed location in the bottom-left portion of the field of view as the viewpoint is redirected from the initial to the subsequent position over time.

In contrast, as illustrated in FIG. 4B, when user 202 redirects display device 204 in the same way for physical-world-anchored augmented content 406, physical-world-anchored augmented content 406 remains in the same place relative to object 402. As shown in FIG. 4B, physical-world-anchored augmented content 406 gets slightly larger and remains at the fixed location near the top left corner of object 402 as the viewpoint is redirected from the initial to the subsequent position over time.

Returning to FIG. 3, each of augmented contents 302 and 304 may be implemented as a viewpoint-anchored augmented content in some instances, a physical-world-anchored augmented content in some instances, or a free-floating or other-anchored augmented content in some instances. In some examples, one or both of augmented contents 302 and 304 may become anchored, or change their anchor modes, under certain circumstances, such as based on where viewpoint 206 is directed within physical world 200. For instance, in one particular implementation, both augmented contents 302 and 304 may remain anchored relative to viewpoint 206 (e.g., at the bottom-left and bottom-right portions of the field of view, respectively, as shown) as user 202 moves viewpoint 206 within anchor region 208. However, if user 202 directs viewpoint 206 outside of anchor region 208, system 100 may begin presenting augmented content 302 and/or 304 in a less evident manner. To present augmented content 302 and/or 304 in the less evident manner, system 100 may present the augmented content less visibly than the evident manner shown in FIG. 3, and/or may change the anchor mode from the viewpoint anchor mode to another mode. As a specific example of mode changing, system 100 may present the augmented content in a physical-world anchor mode (e.g., physical-world anchor mode 400-2).

For example, in some instances, as user 202 moves viewpoint 206 out of anchor region 208, system 100 may direct display device 204 to present the augmented content in the less evident manner by unanchoring the augmented content relative to viewpoint 206. This unanchoring may include ceasing to anchor the augmented content relative to viewpoint 206 in at least one spatial direction (i.e., such that the augmented content does not follow viewpoint 206 in at least that one spatial direction). As used herein, a spatial direction may refer to a translational or a rotational direction of movement in space. As such, when augmented content becomes unanchored from a viewpoint in a particular spatial direction, movements by the viewpoint in that particular spatial direction may no longer cause the augmented content to move accordingly.

In some examples, the ceasing to anchor the augmented content in the at least one spatial direction may be performed by ceasing to anchor the augmented content to viewpoint 206 in all spatial directions, such that the augmented content is no longer anchored to viewpoint 206 in any spatial direction. In other examples, the ceasing to anchor the augmented content in the at least one spatial direction comprises unanchoring the augmented content in less than all spatial directions, such as in only one spatial direction, such that the augmented content does not move in the at least one spatial direction relative to anchor region 208 as viewpoint 206 moves, but does still follow viewpoint 206 as user 202 moves viewpoint 206 in other spatial directions.

Figure 5:
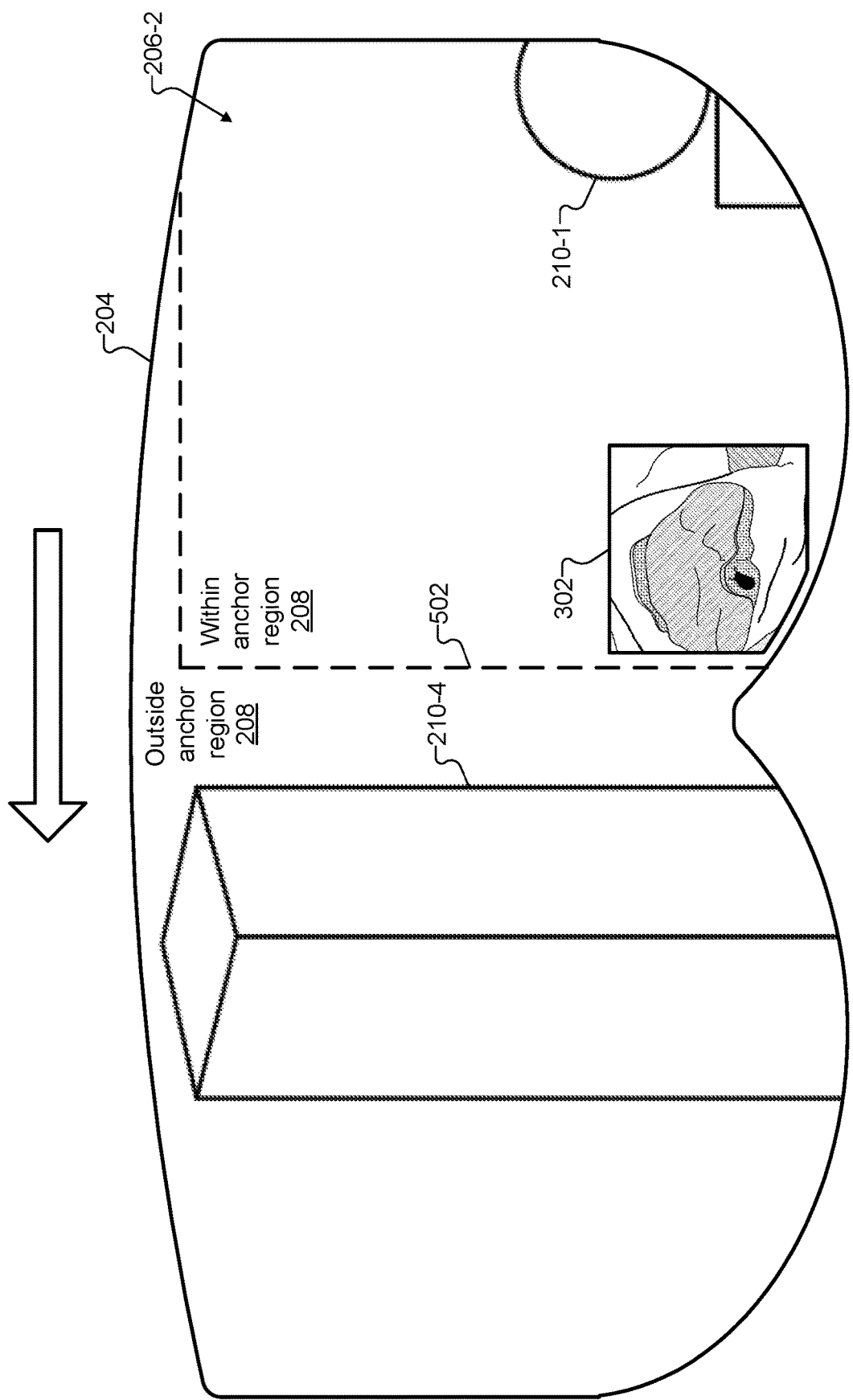
FIG. 5 shows illustrative augmented content that is anchored to a boundary of an anchor region when a viewpoint of a user is directed near the boundary according to principles described herein.

To illustrate one scenario where anchoring may be different for different spatial directions, FIG. 5 shows an illustrative example for when the viewpoint 206-2 is directed near a boundary 502 of anchor region 208. In FIG. 5, augmented content 302 is anchored in a first spatial direction relative to a viewpoint of a user and anchored in a second spatial direction relative to the boundary. In FIG. 5, viewpoint 206-2 represents a moment in time when viewpoint 206 is being moved by user 202 leftward (in accordance with a movement arrow shown above display device 204) so as to move viewpoint 206 across boundary 502 (i.e., so as to move viewpoint 206 from within anchor region 208 to outside of anchor region 208). As described above, for the time while viewpoint 206 remains within anchor region 208, augmented content 302 may be anchored relative to viewpoint 206 in all spatial directions. And, when viewpoint 206 has been directed leftward past boundary 502 of anchor region 208, system 100 may direct display device 204 to change how augmented content 302 is anchored (e.g., change the anchor mode of augmented content 302). Specifically, for example, system 100 may direct display device 204 to cease anchoring augmented content 302 to viewpoint 206, and to begin anchoring augmented content 302 to coordinates in physical world 200 (e.g., coordinates in a world reference frame that does not move with the viewpoint 206).

A change in how augmented content 302 is anchored may affect all or only some of the spatial directions (e.g., lateral, vertical, and depth spatial directions) with respect to which augmented content 302 is anchored. For example, in FIG. 5, augmented content 302 is shown to be anchored, with respect to a lateral (e.g., horizontal) spatial direction, to boundary 502; with this approach, as viewpoint 206 is moved left or right over boundary 502, augmented content 302 remains anchored to boundary 502 and does not leave anchor region 208. At the same time, augmented content 302 may remain anchored, with respect to a vertical spatial direction and/or a depth spatial direction (e.g., distance to boundary 502), to viewpoint 206; with this approach, augmented content 302 is continually displayed near the bottom of the field of view at a constant size as user 202 moves viewpoint 206 over boundary 502. In this way, augmented content 302 may be concurrently anchored in accordance with a viewpoint anchor mode with respect to one or more spatial directions (e.g., the vertical and/or depth spatial directions) while being anchored in accordance with a physical-world anchor mode with respect to one or more other spatial directions (e.g., the lateral and/or the depth spatial directions).

As used herein, augmented content that is anchored to boundary 502 will be considered to be using a form of physical-world anchoring even if boundary 502 is not associated with any particular physical object since anchor region 208 is defined as a region of physical world 200. Additionally, it will be understood that augmented content may be anchored to the anchor region in various ways other than the way shown in FIG. 5. For example, an augmented content may be anchored on the outside of a boundary, anchored so as to be centered on the boundary, anchored with respect to two or more spatial directions (instead of just to the lateral spatial direction such as described above), anchored to a center of the anchor region, anchored in rotation and not anchored in translation, or the like.

In certain implementations or situations, the less evident manner of presenting augmented content may involve presenting the augmented content less visibly. Presenting the augmented content less visibly may be instead of, or in addition to, unanchoring the augmented content relative to the viewpoint in the ways described above. For instance, augmented content may be presented less visibly in any of the ways that will now be described in reference to FIGS. 6-8.

Figure 6:
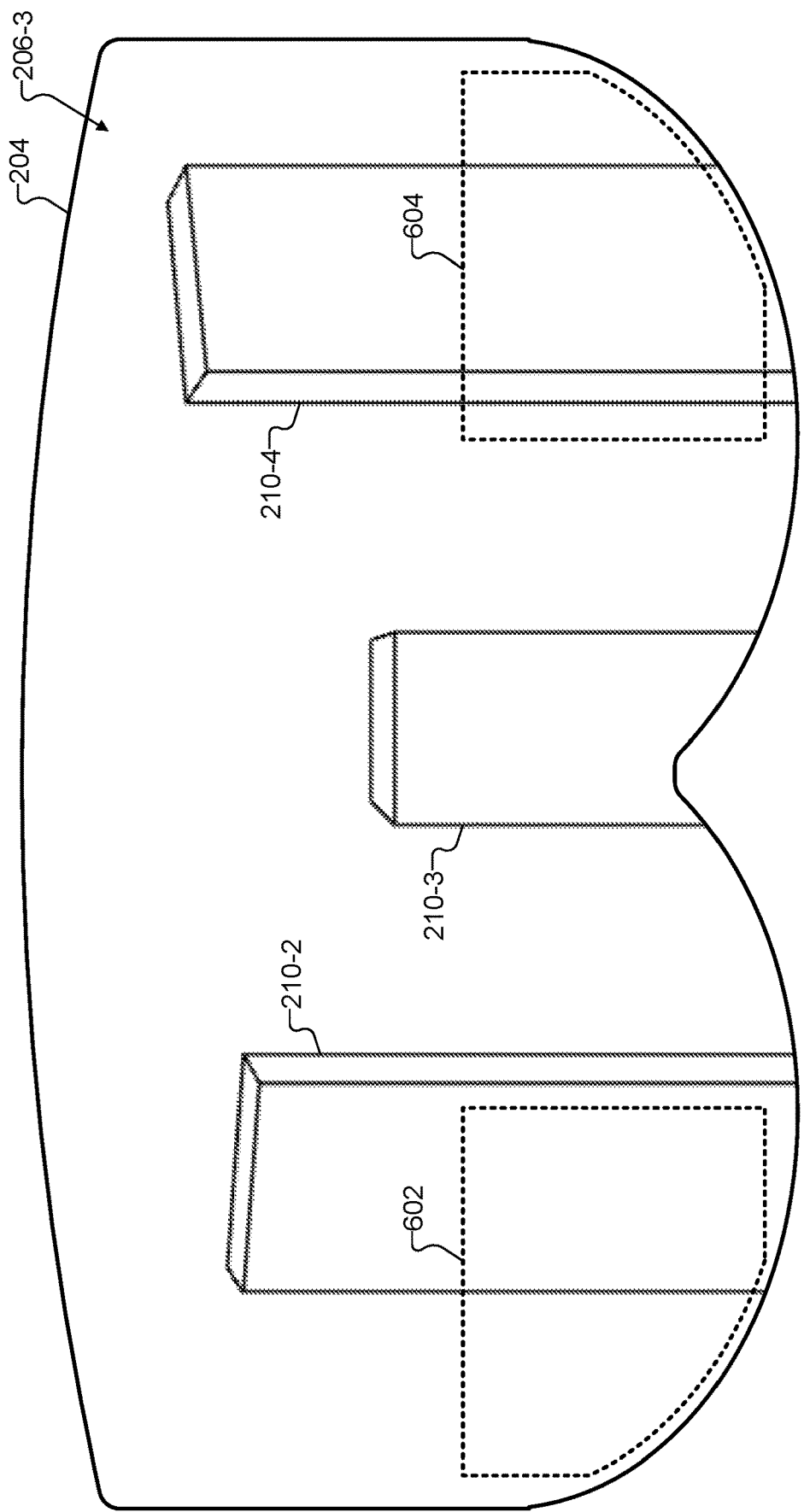
FIGS. 6-8 show various illustrative presentations of augmented content in a less evident manner according to principles described herein.
Figure 7:
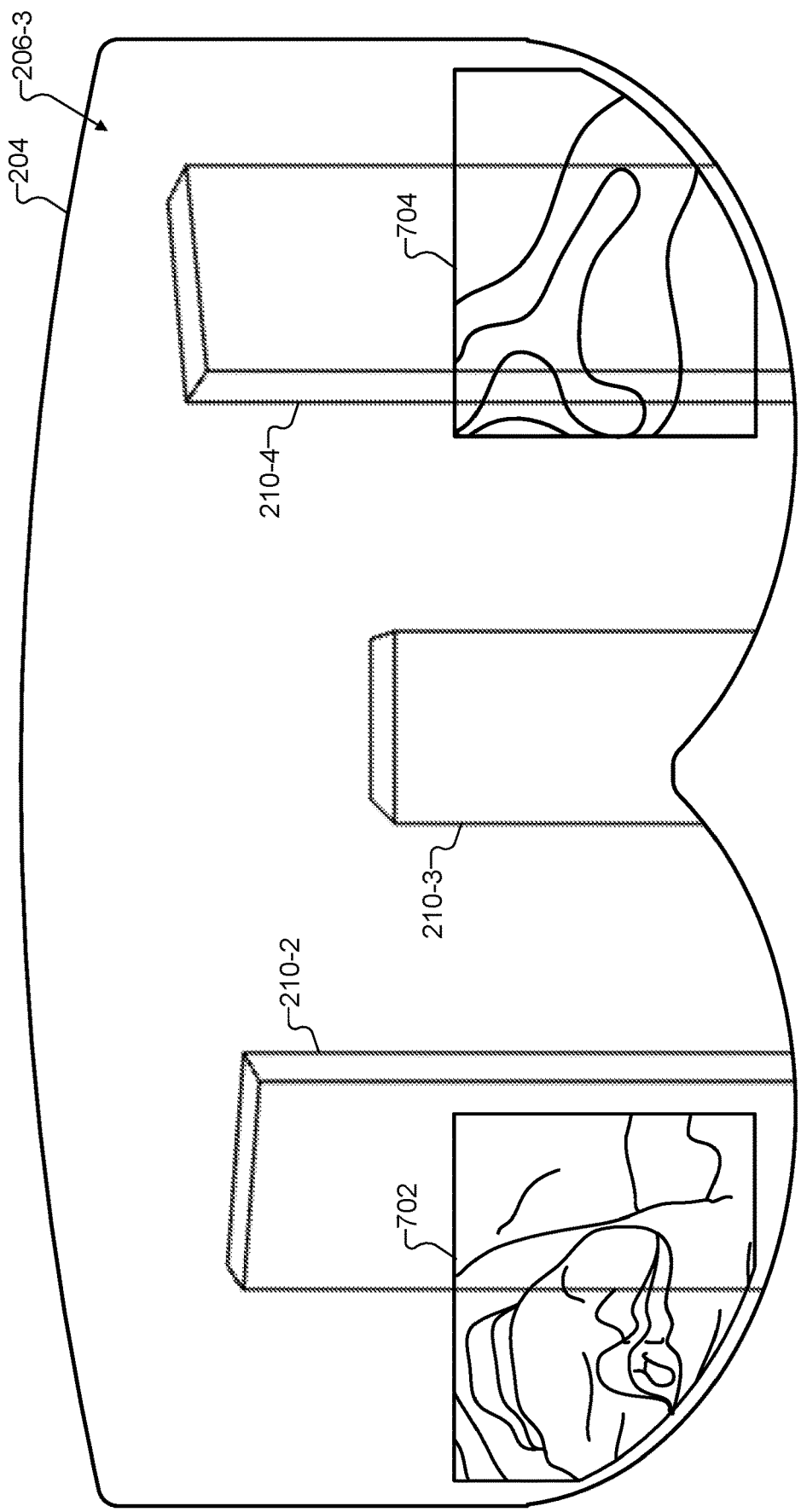
Figure 8:
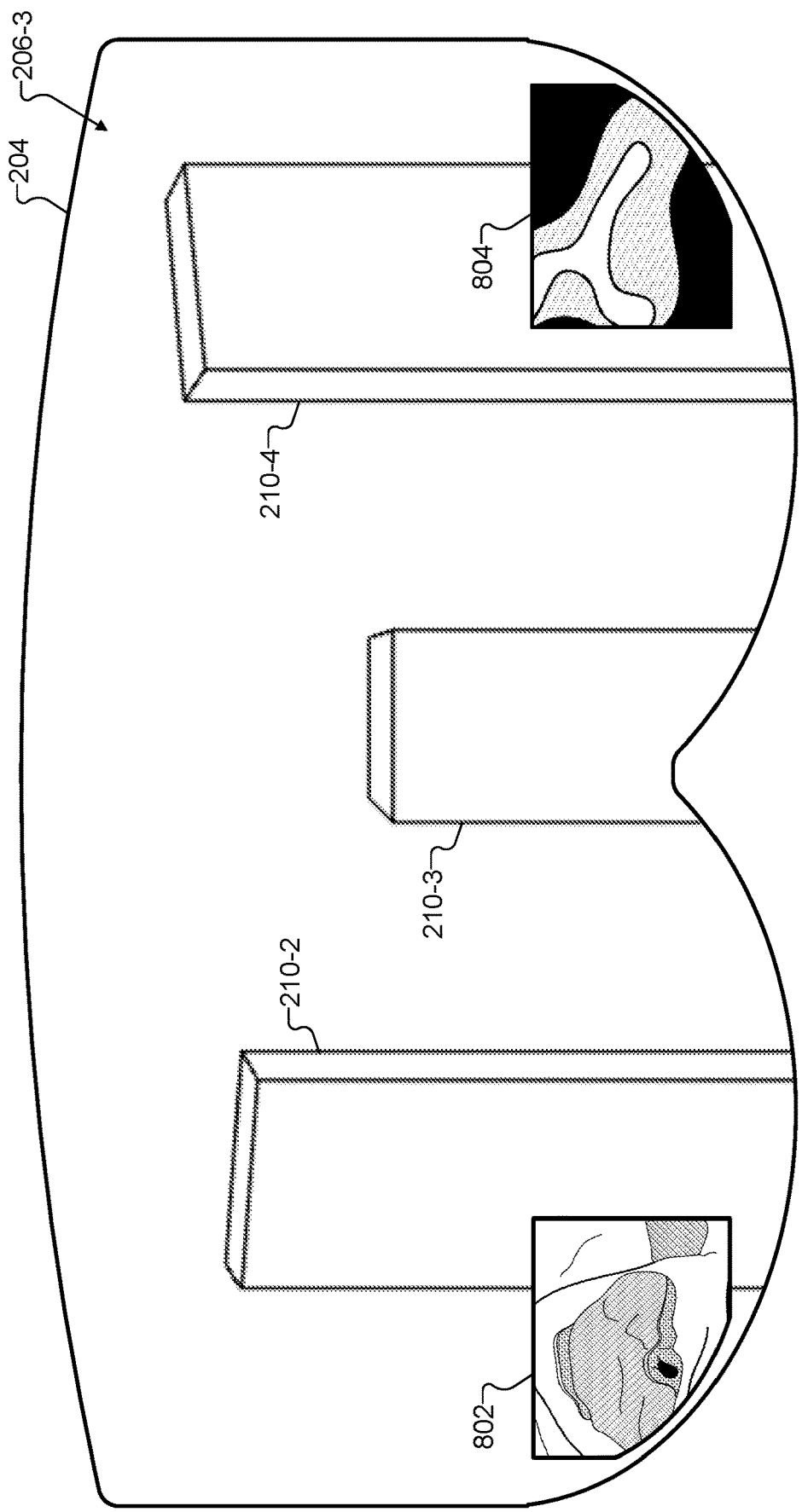

FIGS. 6-8 show various illustrative presentations of augmented content in the less evident manner for viewpoint 206-3, which is directed outside of anchor region 208 in the general direction of objects 210-2 through 210-4 (and not in the direction of object 210-1). In the medical procedure example, viewpoint 206-3 may represent a view associated with a task that is not directly related to the body represented by object 210-1 and in which, as a result, it may not be helpful or desirable for user 202 to be presented with augmented content representative of the internal view of the body in a manner as evident as when viewpoint 206 is directed within anchor region 208. For instance, objects 210-2 through 210-4 may represent other people with whom user 202 may need to converse, a selection of instrumentation that user 202 is tasked with selecting or manipulating, a physical screen that provides different types of information to user 202 than is presented within the augmented content, or the like. Accordingly, FIGS. 6-8 show various illustrative ways that augmented content may be presented in a less evident manner than, for example, the evident manner presented in FIG. 3 for viewpoint 206-1.

FIG. 6 shows that system 100 may direct display device 204 to present augmented content 302 and 304 in the less evident manner by ceasing the presenting of the augmented content altogether (an example of presenting the augmented content less visibly). Specifically, as shown by an empty shape 602 at the bottom-left portion of the field of view where augmented content 302 was previously presented, and by an empty shape 604 at the bottom-right portion of the field of view where augmented content 304 was previously presented, system 100 may direct display device 204 to cease presenting augmented content 302 or 304 (or any other augmented content) while viewpoint 206 is directed outside of anchor region 208.

As another example, FIG. 7 shows that system 100 may direct display device 204 to display augmented content 302 and 304 in the less evident manner by increasing a transparency or a translucency of augmented content 302 and 304 (another example of presenting the augmented content less visibly). Specifically, as shown by an augmented content 702 at the bottom-left portion of the field of view where augmented content 302 was previously presented, and by an augmented content 704 at the bottom-right portion of the field of view where augmented content 304 was previously presented, system 100 may direct display device 204 to adjust the augmented content to be more transparent or translucent when viewpoint 206 is directed outside of anchor region 208 than when viewpoint 206 is directed within anchor region 208. The increased transparency or translucency may decrease an opacity of the augmented content. An example is illustrated by comparing FIG. 3 with FIG. 7. Augmented content 302 and 304 in FIG. 3 are completely opaque and block viewing of physical world 200 behind them, while augmented content 702 and 704 in FIG. 7 are partially transparent or translucent and allow viewing of objects within the physical world 200 behind them.

As another example, FIG. 8 shows that system 100 may direct display device 204 to display augmented content 302 and 304 in the less evident manner by decreasing a size of augmented content 302 and 304 as presented by display device 204 (yet another example of presenting the augmented content less visibly). Specifically, as shown by an augmented content 802 at the bottom-left portion of the field of view where augmented content 302 was previously presented, and by an augmented content 804 at the bottom-right portion of the field of view where augmented content 304 was previously presented, system 100 may direct display device 204 to cause the augmented content to be smaller in size when viewpoint 206 is directed outside of anchor region 208 than when viewpoint 206 is directed within anchor region 208. An example is illustrated by comparing FIG. 3 and FIG. 8. Augmented content 302 and 304 in FIG. 3 are relatively larger, and thus more prominent, while augmented content 802 and 804 in FIG. 8 are relatively smaller, and thus less prominent and more inconspicuous, by comparison.

In other examples, system 100 may direct display device 204 to present augmented content 302 and 304 in the less evident manner by using a combination of the principles illustrated in FIGS. 4-8, or in other manners that make augmented content 302 and 304 less evident. For instance, augmented content may be made less visible by decreasing a brightness property of the augmented content, changing an anchoring of the augmented content (e.g., by moving augmented content to be anchored at a less prominent portion of the field of view, etc.), simplifying or reducing the augmented content (e.g. displaying reduced-color images, outlines instead of full images, abbreviated text or shortened messages, simpler graphics, symbols instead of text, etc.), or the like.

System 100 may transition between presenting augmented content in the evident manner and the less evident manner in an abrupt manner, or in a more gradual manner. Examples of more gradual manners include a slower fading from a more visible display of the augmented content to a less visible display of the augmented content. For example, the system may cause the transition between presenting in the evident and the less evident manners based on an elapsed time since an event has occurred (e.g., since viewpoint 206 has exited or entered anchor region 208), and the change in the presentation of the augmented content can be a complete change between evident and less evident, that occurs immediately after the event has occurred, that occurs after a predetermined period of time has passed after the event has occurred, that occurs more gradually based on the passage of time after the event has occurred, etc. Analogously, change in the presentation of the augmented content can be a complete change between evident and less evident, that occurs as soon as the viewpoint direction, location, velocity direction, velocity magnitude, acceleration direction, acceleration magnitude, etc. meets a threshold or other criteria, or occurs gradually based the approaching, meeting, or exceeding of the threshold or other criteria. As further examples, other instances may use other suitable conditions as may serve a particular implementation.

In certain examples, the presenting by system 100 of the augmented content in the less evident manner may include presenting the augmented content less visibly than the evident manner by varying a visual property of the augmented content based on one or more parameters. Such parameters may include, for example, 1) a distance between a boundary of the anchor region and a location outside the anchor region at which the viewpoint is directed, 2) an elapsed time since the determination that the viewpoint is directed outside of the anchor region, 3) a speed at which the viewpoint is moving with respect to the boundary of the anchor region, or any other parameter as may serve a particular implementation. In this way, the presentation of the augmented content may become increasingly less evident as the parameter(s) change until, in certain implementations, one or more applicable thresholds are met. For example, the presentation may become increasingly less evident (e.g., the transparency or translucency may gradually increase, the size may gradually decrease, etc.) until a certain distance or speed has been reached, a certain time has elapsed, a certain transparency or size has been achieved, or the like.

In some examples, the transition between the evident and less evident manners of presentation may occur as viewpoint 206 approaches an anchor region boundary such as boundary 502 (i.e., such that the transition may be underway or complete by the time the boundary is crossed). In contrast, in other examples, the transition between the evident and less evident manners may occur after viewpoint 206 has crossed the boundary. As such, system 100 may, in certain implementations, define a transition region near the boundary of an anchor region, and the transition region may be used to facilitate various types of smooth transitions between the evident and less evident manners of augmented content presentation, including smooth transitions between a viewpoint anchor mode and a physical-world anchor mode used for anchoring augmented content.

As an example of such a transition, augmented content may be positioned, relative to viewpoint 206, based on a weighted linear combination of the respective positions, poses, motion coordinates, and/or other such characteristics of the viewpoint and an anchor region boundary. In this example, as viewpoint 206 enters the transition region, the augmented content is anchored entirely to the viewpoint (e.g., using a viewpoint anchor mode), while, by the time viewpoint 206 exits the transition region, the augmented content is anchored entirely to the boundary of the anchor region (e.g., using a physical-world anchor mode). This type of transitioning may be implemented with respect to one or more spatial directions, and may have the visual effect of slowing down the augmented content or gradually decoupling it from the viewpoint as the content passes through the transition region.

As another example of a transition, system 100 may scale the speed of motion of the augmented content relative to the anchor region boundary as the augmented content moves through the transition region, bringing the augmented content to rest (i.e., the relative speed reaching zero) when viewpoint 206 fully exits the transition region. In still other implementations, a virtual spring force may be simulated to tether the augmented content to the anchor region boundary as viewpoint 206 passes through the transition region, or another suitable transition may be employed.

Once system 100 has determined that viewpoint 206 is directed outside of anchor region 208 and has accordingly directed display device 204 to present the augmented content in the less evident manner, system 100 may continue to monitor how user 202 directs viewpoint 206 and further change the presentation of the augmented content in response. For example, subsequent to the determination that viewpoint 206 is directed outside of anchor region 208, system 100 may determine that viewpoint 206 is again directed within anchor region 208. In response to this determination that viewpoint 206 is again directed within anchor region 208, system 100 may direct display device 204 to present the augmented content in the evident manner or another evident manner. In certain examples, system 100 may return to presenting in the evident manner instantaneously, while, in other examples, the presenting may occur gradually using a transition period or transition region. Such a transition period or region may be similar but inverse to those described above.

The examples described above in relation to FIGS. 3-8 have related to augmented content that is presented in different ways (e.g., according to an evident manner, according to a less evident manner, etc.) based on how user 202 directs viewpoint 206 (e.g., by moving display device 204). It will be understood that, in certain implementations and/or in certain scenarios encountered by a given implementation, system 100 may direct display device 204 to present augmented content in either the evident or less evident manner based on various criteria other than the direction of viewpoint 206 with respect to anchor region 208.

For instance, in various examples, system 100 may determine that an event occurring or an action performed by user 202 while viewpoint 206 is directed outside anchor region 208 is associated with displaying the augmented content in the evident manner; in response to this determination, system 100 may direct display device 204 to display the augmented content in the evident manner instead of the less evident manner associated with viewpoint 206 being directed outside of anchor region 208. Further, system 100 may determine that an event occurring or an action performed by user 202 while viewpoint 206 is directed within anchor region 208 is associated with displaying the augmented content in the less evident manner; in response to this determination, system 100 may direct display device 204 to display the augmented content in the less evident manner instead of the evident manner associated with viewpoint 206 being directed within anchor region 208.

Implementations may have no definition of events or actions that modify the display of the augmented content in the evident or less evident manner. Various implementations that do have such definitions differ in what actions or events cause such modification. Examples of events and actions that may cause the augmented content to be presented in a manner mismatching those described above that cause the augmented content to be presented in an evident manner when viewpoint 206 is directed outside the anchor region, or to be presented in a less evident manner when viewpoint 206 is directed within the anchor region) include the following: a fault of equipment used in the procedure taking place in physical world 200, an emergency event in physical world 200, an unexpected movement or action by a system used in the medical procedure, an unexpected event or action, a command issued by user 202 or some other personnel involved in the procedure, a beginning or continuing performance of the procedure or a particular stage of the procedure, manipulating a body or a tool in a work site for the procedure, manipulation of a tool within the body, current usage of a particular tool, or achievement of a particular event or milestone of the procedure.

In implementations of system 100 (e.g., implementations such as described below in relation to FIG. 10) that include a robotic manipulator arm configured to support a tool, the events or actions may include removing the tool from the robotic manipulator arm, attaching the tool to the manipulator arm, manipulating the tool, powering the tool up, powering the tool down, connecting the tool to a control system or power supply, or another such tool-related action. In still other examples, the events or action may involve commands issued by user 202, such as a voice, gestural, or input device command associated with the display of the augmented content.

Additional examples of events and actions that may cause system 100 to present the augmented content in a manner that mismatches the viewpoint 206 include: a beginning or continuance of a certain phase or stage of the medical procedure (e.g., in an example involving a computer-assisted medical system having a robotic manipulator arm, a positioning of a manipulator assembly or a mounting of the manipulator arm, a docking of the manipulator arm, a physical or electrical coupling of an instrument with the manipulator arm, an electrical coupling of an instrument with the computer-assisted medical system, etc.), a change in a state of the system, an external manipulation (such as by 202) of the manipulator arm, a placing of the manipulator arm to a clutched mode, an installation or re-installation of an instrument, a connection of cables or accessories to the system, a collision or impending collision between instruments or manipulator arms, a collision or impending collision of a robotic arm or instrument with a person (e.g., user 202, a patient, an assistant, etc.), an instrument error, an active insertion of operation of an instrument, a performance of tasks unrelated to the augmented content, and so forth.

In a specific example, system 100 may determine that user 202 moves viewpoint 206 at a rate greater than a threshold rate, and, in response to this determination, direct display device 204 to present the augmented content in the less evident manner even if viewpoint 206 is directed within anchor region 208, For a head-mounted display device 204 example, if user 202 turns quickly or swivels his or her head quickly, viewpoint 206 may quickly pass through part or all of anchor region 208. In such an instance, the direction of viewpoint 206 may be incidental and/or temporary, and user 202 may not intend to view anchor region 208, and instead intend to look past anchor region 208 or to something else that is outside of anchor region 208. Based on the speed of the of the head turn (e.g., based on the movement rate being greater than the threshold rate), system 100 may determine that. Thus, in some instances, system 100 may direct display device 204 to begin or continue presenting the augmented content in the less evident manner while a speed of movement of display device 204, viewpoint 206, or user 202 is determined to be higher than a threshold speed. This may be the case even if viewpoint 206 is directed within anchor region 208.

Some of the examples above discuss instances where augmented content is automatically presented in certain ways based on determinations made by system 100. In some examples, system 100 may also present augmented content based at least in part on manual indications by user 202 or other personnel that directly or indirectly indicate how augmented content is desired to be presented by display device 204. For example, user 202 or other personnel may indicate his or her preference regarding the presentation of augmented content in the evident or less evident manner through any appropriate input technique, and system 100 may present the augmented content in accordance with the input of user 202 or other personnel. Example input techniques include button presses, voice commands, gestural input, and so forth.

In various examples, anchor region 208 may be automatically defined by system 100, or partially or fully user defined (e.g., by user 202 or other personnel) using any type of anchor region definition technique as may serve a particular implementation. For example, a user may define the anchor region using movement of an eye gaze, the head, a hand, or some other body part or tool controlled by the user, to indicate region corners, edges, or entire boundaries. In some other examples, the user may define some (but not necessarily all) of the boundaries of an anchor region using assistance from system 100, and system 100 may define other boundaries of the anchor region automatically. For instance, system 100 may receive user inputs such as those described above to define certain boundaries, or to identify regions in the physical space that should not be obscured by the augmented view, and then system 100 may compute an optimal anchor region based on this and other information. In other examples, a user may select a preset anchor region from a library of preset anchor regions provided by system 100.

As a further, specific example, certain boundary segments of an anchor region may be defined automatically by system 100 based on operating conditions (e.g., a lower boundary may be defined by system 100 as a surface based on a site of a medical procedure or a body receiving the medical procedure) while other boundary portions of the anchor region may be user-defined (e.g., an upper boundary and one or more lateral boundaries may be surface portions defined based on user input).

Example operating conditions that may be used to aid system 100 in defining an anchor region include: the type of medical procedure that is being performed, the amount and/or location of space left free around equipment (e.g. a manipulator system involved in the procedure), the amount and/or location of the body undergoing the procedure or another object in the physical world, and/or any of the examples previously discussed. Moreover, in some examples where the medical procedure is performed in a series of operational stages, system 100 may automatically redefine the anchor region during the medical procedure based on the current operational stage of the medical procedure. For example, in response to the medical procedure transitioning from a first operational stage to a second operational stage, system 100 may automatically redefine the anchor region from a first region associated with the first operational stage to a second region associated with the second operation stage; the first region and the second region may be the same, or be distinct from each other, depending on various considerations including operational stages. Similarly, system 100 may automatically redefine the anchor region based on where a user or one or more other people are positioned with respect to the body, based on current spatial characteristics of manipulator arms or instruments being used to perform the medical procedure, or based on other suitable criteria as may serve a particular implementation.

FIG. 2 depicts an anchor region 208 consisting of a single, box-like shape. Other instances may utilize anchor regions of other shapes, such as spheres, ellipsoids, cylinders, polyhedrons, shapes formed with any combination of curved or planar surfaces, etc. Anchor regions may comprise any number of symmetric or asymmetric, or convex or concave portions. As an example, in some instances, the anchor region is defined based on the volume of an object in the physical world. As a specific example, an anchor region defined to surround a patient on an operating table may be defined by offsetting the outer surfaces of the patient and operating table outwards, and then connecting them. To illustrate further example anchor regions, FIGS. 9A-9D show various illustrative aspects of various anchor regions that may be defined within a physical world (e.g., physical world 200) in various implementations. It will be understood that the anchor regions of FIGS. 9A-9D represent anchor regions in three-dimensional in space, although FIGS. 9A-9D depict a cross section of each respective anchor region for illustrative convenience. Each of FIGS. 9A-9D will now be described in more detail.

Figure 9B:
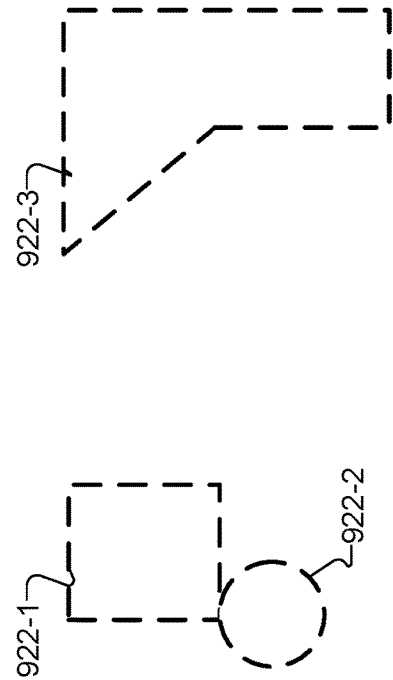
FIGS. 9A-9D show various illustrative aspects of anchor regions that are defined within the physical world according to principles described herein.
Figure 9D:
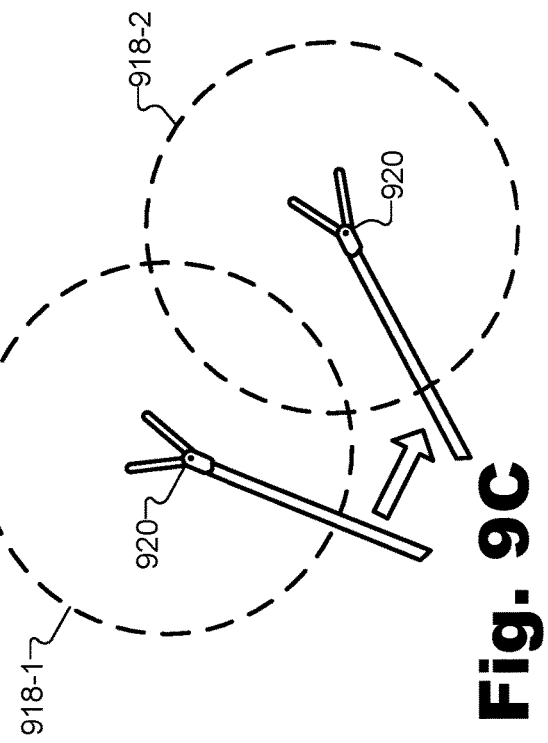
Figure 9A:
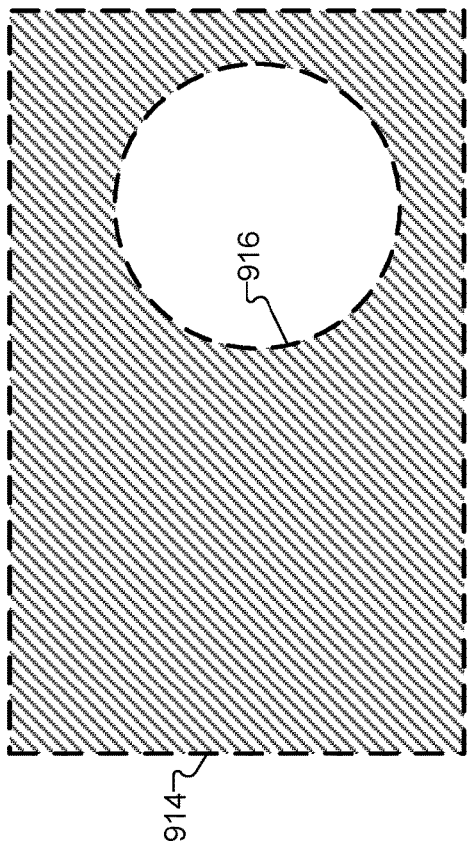

FIG. 9A illustrates an anchor region 902 that is associated with a medical area at which a medical procedure is being performed on a body 904. Body 904, as illustrated, is resting on an operating table 906. In the example of FIG. 9A, the medical procedure is shown to be performed using an instrument 908 that enters body 904 at an entry location 910 on body 904 to operate internally within body 904. For example, entry location 910 may be an incision into which is inserted a cannula (not shown). In this example, anchor region 902 may be defined based on the site for the medical procedure. For instance, anchor region 902 may be defined based on entry location 910. One example way this may be done is for anchor region 902 to be automatically defined as the region within a particular distance 912 (i.e., a radius) from entry location 910. Accordingly, based on entry location 910 and distance 912 (e.g., both of which may either be provided by a user or determined automatically using default values or in other ways described herein), system 100 may efficiently and automatically define anchor region 902 to incorporate a suitable area around where the medical procedure is being performed.

In the same or other examples, the system (e.g. system 100) may generate anchor regions (e.g., anchor region 902) in any appropriate way as may serve a particular implementation. For instance, a robotic system in the physical world (e.g. physical world 200) may comprise one or more manipulator arms, where each manipulator arm has a remote center of motion about which the manipulator arm pivots during operation. The real-time location of a remote center of a manipulator arm may be determined in any appropriate way, including based on the geometric parameters and real-time kinematic information of the manipulator arm, along with registration information that registers the robotic system to the physical world, or the display device (e.g. display device 204), or another reference. In some instances, the remote center(s) of motion are generally collocated with entry locations (e.g. entry location 910). In some instances, the system bases the anchor region definition on at least the location(s) of remote center(s) of motion. Another potential usage of kinematic information is to position an anchor region relative to the working direction of the procedure (e.g., based on a physical configuration of one or more manipulator arms or tools supported by the manipulator arm(s), the pointing direction or location of visual focus of an image capture device such as an endoscope, etc.). In some examples, the image capture device direction may be used to define an initial position of the anchor region, and that initial position may be modified or confirmed by the user through user input.

In still other examples, a system (e.g. system 100) may generate an anchor region (e.g., anchor region 902) based on other or additional factors. Example factors include: where a user (e.g., user 202) is located, an anticipated shape of the procedure space (e.g., a space around operating table 906), one or more devices around operating table 906, an identification of space left open near operating table 906, a user-preferred region of interest, a machine-learning model based on procedure type, user preferences, other data related to the procedure, and any other suitable factor or combination thereof.

FIG. 9B illustrates an anchor region 914 (the shaded area) that is defined to include a first region of the physical world (i.e., a box-shaped region 914 containing an spherical region that is a non-anchor region 916) that fully encloses a second region of the physical world (La, the spherical region that is a non-anchor region 916 in FIG. 9B). The non-anchor region 916 is not part of anchor region 914 (and is thus not shaded). In certain implementations, the anchor region may comprise a region containing any number and shape of internal non-anchor regions. In some implementations, the anchor region 914 may operate in a same or similar manner as described above for anchor region 208 (aside from the shape differences). In other implementations, anchor region 914 may operate in a different manner than anchor region 208. For example, the non-anchor region 916 may be a non-occludable region. As used herein, a non-occludable region is a region of the physical world that is not to be occluded by certain augmented content, or not to be occluded by any augmented content. Examples of regions that user 202 may want to assign as non-occludable regions include: regions containing a physical monitor or a person (e.g., an assistant or nurse for a medical procedure), regions of special import for the procedure (e.g., a region immediately around an entry location such as entry location 910 in FIG. 9A), or any other suitable regions where user 202 wants to retain visibility. In some instances, the user defines the non-occludable regions. In some instances, the system semi-automatically defines non-occludable regions, such as by identifying, and presenting for selection or confirmation, potential non-occludable regions based on operating conditions or other factors. In some instances, the system automatically defines the non-occludable regions based on operating conditions or other factors.

As a specific example, in some instances, when the augmented content is anchored relative to viewpoint 206 and user 202 moves viewpoint 206 such that the augmented content would overlap a non-occludable region (e.g. region 916), the system (e.g., system 100) may direct display device 204 not to display the augmented content in the non-occludable region. For example, system 100 may direct display device 204 to temporarily unanchor the augmented content from viewpoint 206 to avoid occluding the non-occludable region with the augmented content. As a specific example, system 100 may cause the augmented content to be anchored just outside the non-occludable region, at the location where the augmented content would have entered the non-occludable region based on the viewpoint 206 direction, when the augmented content would overwise be within the non-occludable region based on the direction of viewpoint 206. While the non-occludable region implemented by non-anchor region 916 is shown to be enclosed by anchor region 914, it will be understood that certain implementations of non-occludable regions may be defined otherwise. For example, a non-occludable region may be defined adjacent to an anchor region rather than enclosed by the anchor region, in an area remote from any anchor regions, etc. Additionally, it will be understood that certain non-occludable regions may move independently within the physical world. For example, a non-occludable region associated with a face of a person in the physical world may move as the person moves about in the physical world.

Figure 9C:
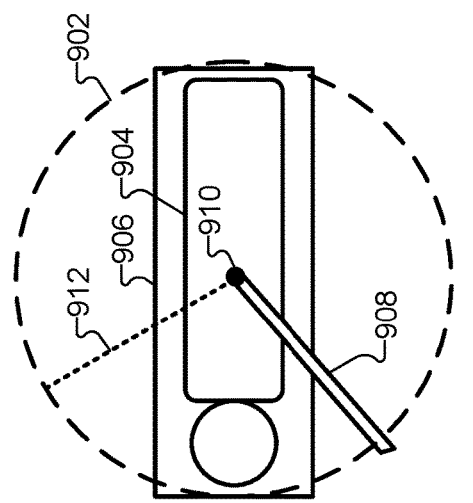

FIG. 9C illustrates an anchor region 918 that is shown at two different moments in time. At a first moment in time, anchor region 918 is labeled as anchor region 918-1, and at a second moment in time, anchor region 918 is labeled as anchor region 918-2. In FIG. 9C, anchor region 918 is shown to be referenced to an object 920 (illustrated in this example as a tip of an instrument) in the physical world. As such, anchor region 918 is shown to be a dynamic anchor region that moves, together with object 920, in the physical world. As shown, when object 920 translates and reorients from a first position to a second position at the two different points in time (and as indicated by the arrow), anchor region 918 is redefined from being anchor region 918-1 to being anchor region 918-2. It will be understood that any object in the physical world may be used to provide a reference for an anchor region such as anchor region 918. Examples of such objects include part or all of: a manipulator arm, a body for a procedure, a tool, an operating table, a piece of equipment, a person, etc.

FIG. 9D illustrates an anchor region 922 that includes a plurality of physically separate sub-regions labeled 922-1 through 922-3 in the physical world. In an example such as shown in FIG. 9D, each sub-region of anchor region 922 may be treated similarly to the anchor regions described above (e.g., anchor region 208). Thus, the various principles described above for other anchor regions in this disclosure may also apply to the sub-regions of a multi-part anchor region such as anchor region 922. As a specific example, a system (e.g. system 100) may determine that a viewpoint of a user is directed within one sub-region of anchor region 922 and, in response to this determination, the system may direct a display device to present augmented content in an evident manner if the viewpoint is directed within a sub-region of anchor region 922, or a less evident manner if the viewpoint is not direction within any sub-regions of anchor region 922.

As shown in FIG. 9D, different sub-regions in a multi-part anchor region such as anchor region 922 may be of different shapes, and also be spatially separated (see, e.g., sub-regions 922-1 and 922-3) or spatially connected to one another (see, e.g., sub-regions 922-1 and 922-2).

Additionally, in certain examples, one or more anchor regions may be shared between multiple users who are located in different places in the physical world. For example, each user may set up his/her own anchor region(s) and then may share some or all of these anchor region(s) as appropriate, such as sharing an anchor region when assisted by others on the task for which the anchor region is set up. In such examples, system 100 may detect that a first user of a first display device shares an anchor region with a second user of a second display device. System 100 may determine that a viewpoint of the second user is directed within the anchor region of the first user and direct, in response to that determination, the second display device to present augmented content to the second user in the evident manner. Additionally, system 100 may later determine that the viewpoint of the second user is directed outside of the anchor region shared by the first user, and not directed within that anchor region and, in response, may direct the second display device to present the augmented content to the second user in the less evident manner.

Figure 10:
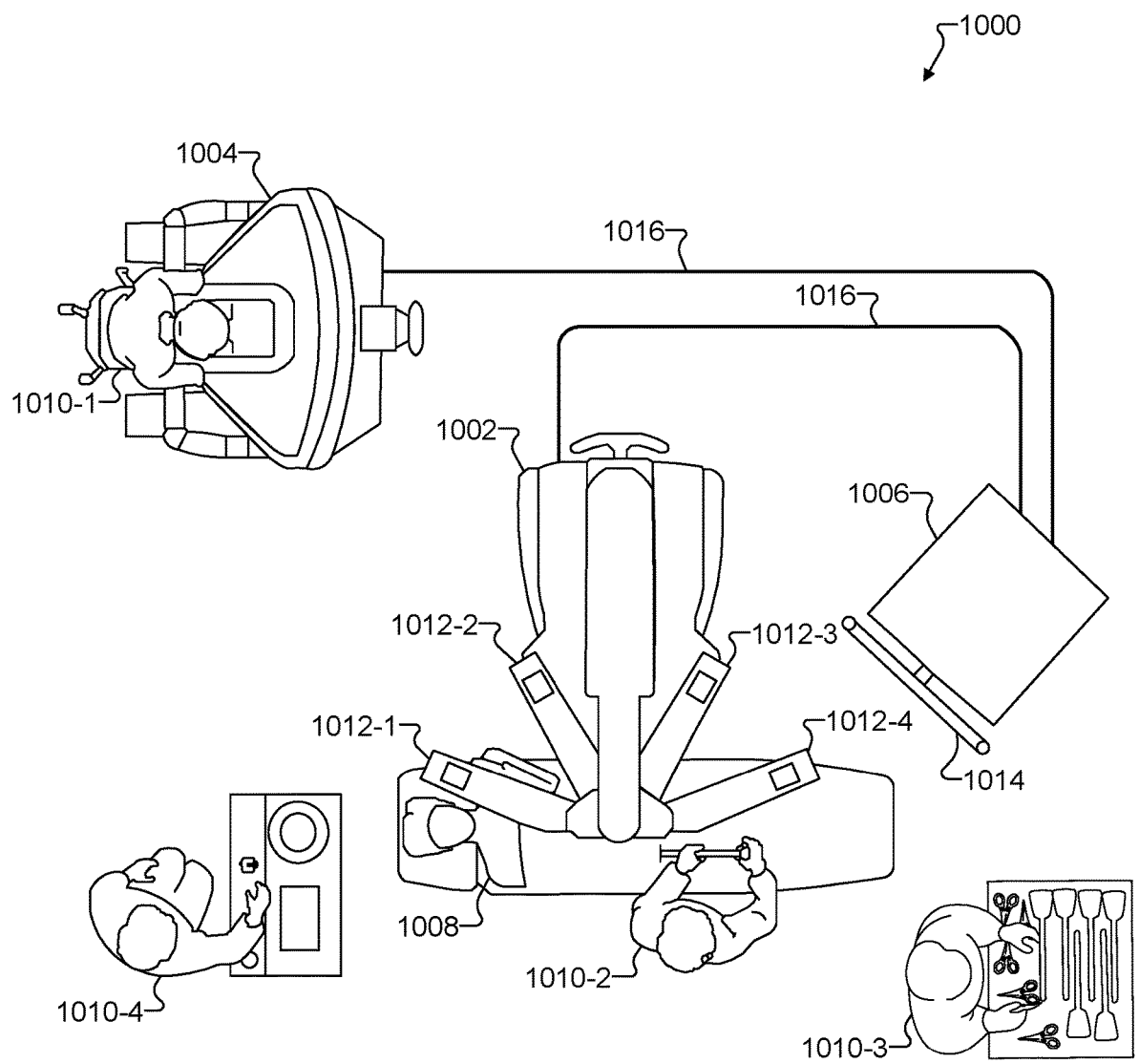
FIG. 10 shows an illustrative computer-assisted medical system according to principles described herein.

To more specifically illustrate a particular medical procedure example, FIG. 10 shows an illustrative computer-assisted medical system 1000 ("medical system 1000") that may be used to perform various types of medical procedures including surgical and/or non-surgical procedures. As shown, medical system 1000 may include a manipulator assembly 1002 (a manipulator cart is shown in FIG. 10), a user control system 1004, and an auxiliary system 1006, all of which are communicatively coupled to each other. Medical system 1000 may be utilized by a medical team to perform a computer-assisted medical procedure or other similar operation on a body of a patient 1008 or on any other body as may serve a particular implementation. As shown, the medical team may include a first user 1010-1 (such as a surgeon for a surgical procedure), a second user 1010-2 (such as a patient-side assistant), a third user 1010-3 (such as another assistant, a nurse, a trainee, etc.), and a fourth user 1010-4 (such as an anesthesiologist for a surgical procedure), all of whom may be collectively referred to as "users 1010," and each of whom may control, interact with, or otherwise be a user of medical system 1000 and/or an implementation of system 100. More, fewer, or alternative users may be present during a medical procedure as may serve a particular implementation. For example, team composition for different medical procedures, or for non-medical procedures, may differ and include users with different roles.

While FIG. 10 illustrates an ongoing minimally invasive medical procedure such as a minimally invasive surgical procedure, it will be understood that medical system 1000 (or a medical system replacing medical system 1000 in FIG. 10) may similarly be used to perform open medical procedures or other types of operations. For example, operations such as exploratory imaging operations, mock medical procedures used for training purposes, and/or other operations may also be performed.

As shown in FIG. 10, manipulator assembly 1002 may include one or more manipulator arms 1012 (FIG. 10 shows manipulator assembly 1002 as including a plurality of robotic manipulator arms 1012 (e.g., arms 1012-1 through 1012-4)) to which one or more instruments may be coupled (FIG. 10 shows a plurality of instruments). The instruments may be used for a computer-assisted medical procedure on patient 1008 (e.g., in a surgical example, by being at least partially inserted into patient 1008 and manipulated within patient 1008). While manipulator assembly 1002 is depicted and described herein as including four manipulator arms 1012, it will be recognized that manipulator assembly 1002 may include a single manipulator arm 1012 or any other number of manipulator arms as may serve a particular implementation. Additionally, it will be understood that, in some examples, one or more instruments may be partially or entirely manually controlled, such as by being handheld and controlled manually by a person. For instance, these partially or entirely manually controlled instruments may be used in conjunction with, or as an alternative to, computer-assisted instrumentation that is coupled to manipulator arms 1012 shown in FIG. 10.

During the medical operation, user control system 1004 may be configured to facilitate teleoperational control by user 1010-1 of manipulator arms 1012 and instruments attached to manipulator arms 1012. To this end, user control system 1004 may provide user 1010-1 with imagery of an operational area associated with patient 1008 as captured by an imaging device.

To facilitate control of instruments, user control system 1004 may include a set of master controls. These master controls may be manipulated by user 1010-1 to control movement of the manipulator arms 1012 or any instruments coupled to manipulator arms 1012.

Auxiliary system 1006 may include one or more computing devices configured to perform auxiliary functions in support of the medical procedure, such as providing insufflation, electrocautery energy, illumination or other energy for imaging devices, image processing, or coordinating components of medical system 1000.

In some examples, auxiliary system 1006 may be configured with a display monitor 1014 configured to display one or more user interfaces, or graphical or textual information in support of the medical procedure. In some instances, display monitor 1014 may be implemented by a touchscreen display and provide user input functionality. Augmented content provided by a region-based augmentation system may be similar, or differ from, content associated with display monitor 1014 or one or more display devices in the operation area (not shown).

As will be described in more detail below, system 100 may be implemented within or may operate in conjunction with medical system 1000. For instance, in certain implementations, system 100 may be implemented entirely by one or more display devices associated with individual users 1010.

Manipulator assembly 1002, user control system 1004, and auxiliary system 1006 may be communicatively coupled one to another in any suitable manner. For example, as shown in FIG. 10, manipulator assembly 1002, user control system 1004, and auxiliary system 1006 may be communicatively coupled by way of control lines 1016, which may represent any wired or wireless communication link as may serve a particular implementation. To this end, manipulator assembly 1002, user control system 1004, and auxiliary system 1006 may each include one or more wired or wireless communication interfaces, such as one or more local area network interfaces. Wi-Fi network interfaces, cellular interfaces, and so forth.

Figure 11:
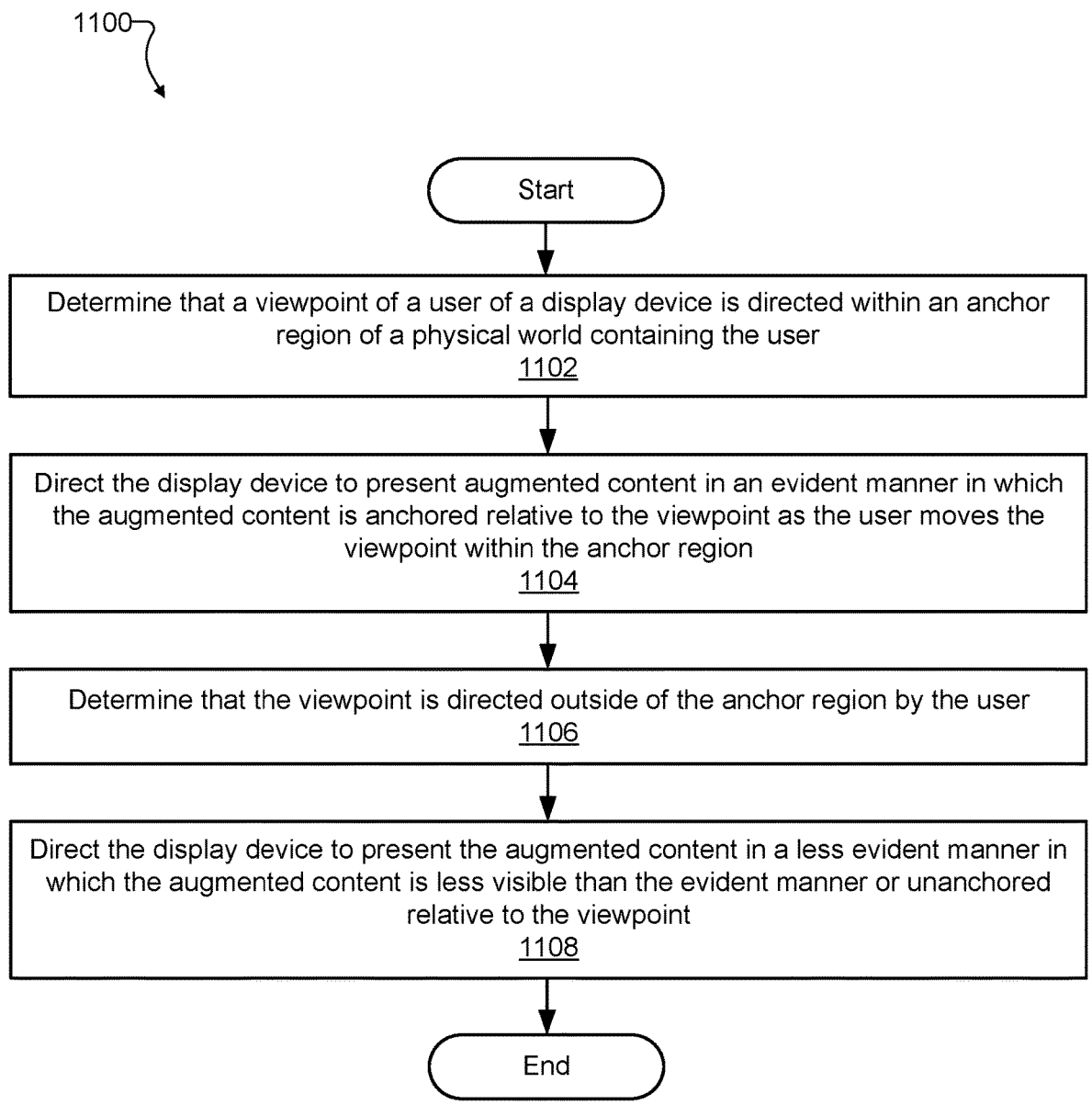
FIG. 11 shows an illustrative method for region-based presentation of augmented content to a user according to principles described herein.

FIG. 11 shows an illustrative method 1100 for region-based presentation of augmented content. While FIG. 11 shows illustrative operations according to one embodiment, other embodiments may omit, add to, reorder, and/or modify any of the operations shown in FIG. 11, One or more of the operations shown in FIG. 11 may be performed by a region-based augmentation system such as system 100, any components included therein, and/or any implementation thereof.

In operation 1102, a region-based augmentation system may determine that a viewpoint of a user of a display device is directed within an anchor region of a physical world containing the user. Operation 1102 may be performed in any of the ways described herein.

In operation 1104, the region-based augmentation system may direct the display device to present augmented content in an evident manner. For example, the region-based augmentation system may direct the display device to present the augmented content in the evident manner in response to the determination in operation 1102 that the viewpoint is directed within the anchor region. In operation 1104, the evident manner in which the augmented content is presented may include anchoring the augmented content relative to the viewpoint such that the augmented content follows the viewpoint as the user moves the viewpoint with the anchor region. Operation 1104 may be performed in any of the ways described herein.

In operation 1106, the region-based augmentation system may determine that the viewpoint is directed outside of the anchor region by the user. Operation 1106 may be performed in any of the ways described herein.

In operation 1108, the region-based augmentation system may direct the display device to present the augmented content in a less evident manner than displayed in operation 1104. For example, the region-based augmentation system may present the augmented content in the less evident manner in response to the determination in operation 1106 that the viewpoint is directed outside of the anchor region. In operation 1108, the presenting of the augmented content in the less evident manner may include presenting the augmented content less visibly than the evident manner of operation 1104 and/or unanchoring the augmented content relative to the viewpoint. Operation 1108 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform any functionality described herein (e.g., including any of the operations of method 1100 described above). Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Examples of non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Examples of volatile storage media include, but are not limited to, RAM (e.g., dynamic RAM).

In some examples, any of the systems and/or other components described herein may be implemented by a computing device including one or more processors, storage devices, input/output modules, communication interfaces, buses, infrastructures, and so forth. For instance, memory 102 of system 100 may be implemented by a storage device of the computing device, and processor 104 of system 100 may be implemented by one or more processors of the computing device. In other examples, the systems and/or other components described herein may be implemented by any suitable non-transitory computer-readable medium storing instructions that, when executed, direct a processor of such a computing device to perform methods and operations described herein.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to perform operations comprising:
   determining that a viewpoint of a user of a display device is directed within an anchor region of a physical world containing the user, the anchor region having a defined boundary;
   directing, in response to the determination that the viewpoint is directed within the anchor region, the display device to present augmented content in an evident manner, wherein the evident manner comprises anchoring the augmented content relative to the viewpoint, such that the augmented content follows the viewpoint as the user moves the viewpoint within the anchor region;
   determining that the viewpoint is directed outside of the anchor region by the user, the determining that the viewpoint is directed outside of the anchor region comprising determining that the viewpoint moves across the defined boundary of the anchor region; and
   directing, in response to the determination that the viewpoint is directed outside of the anchor region, the display device to present the augmented content in a less evident manner, wherein presenting the augmented content in the less evident manner comprises: presenting the augmented content less visibly than the evident manner or unanchoring the augmented content relative to the viewpoint.

2. The system of claim 1, wherein presenting the augmented content in the less evident manner comprises presenting the augmented content less visibly by:
   ceasing the presenting of the augmented content;
   increasing a transparency or a translucency of the augmented content; or
   decreasing a size of the augmented content as presented by the display device.

3. The system of claim 1, wherein presenting the augmented content in the less evident manner comprises unanchoring the augmented content relative to the viewpoint by:
   ceasing to anchor the augmented content relative to the viewpoint in at least one spatial direction, such that the augmented content does not follow the viewpoint in the at least one spatial direction.

4. The system of claim 1, wherein presenting the augmented content in the less evident manner comprises presenting the augmented content less visibly than the evident manner by varying a visual property of the augmented content based on at least one parameter selected from the group consisting of:
   a distance between the anchor region and a location outside the anchor region at which the viewpoint is directed;
   an elapsed time since the determination that the viewpoint is directed outside of the anchor region; and
   a speed at which the viewpoint is moving with respect to the anchor region.

5. The system of claim 1, wherein the operations further comprise, subsequent to the determination that the viewpoint is directed outside of the anchor region:
   determining that the viewpoint is again directed within the anchor region; and directing, in response to the determination that the viewpoint is again directed within the anchor region, the display device to present the augmented content in the evident manner.

6. The system of claim 1, wherein a medical procedure is performed in the physical world, and wherein the operations further comprise:
defining the anchor region based on a site for the medical procedure.

7. The system of claim 6, wherein defining the anchor region based on the site for the medical procedure comprises defining the anchor region based on at least one parameter selected from the group consisting of:
an entry location for an instrument used in the medical procedure, and
a direction in which an image capture device used for the medical procedure is directed.

8. The system of claim 1, wherein a medical procedure is performed in the physical world, wherein the medical procedure comprises a first operational stage and a second operational stage, and wherein the operations further comprise:
automatically redefining, in response to the medical procedure transitioning from the first operational stage to the second operational stage, the anchor region from a first region to a second region, the first region being associated with the first operational stage and the second region being associated with the second operational stage, the second region different from the first region.

9. The system of claim 1, wherein the anchor region is referenced to an object in the physical world, and moves with the object.

10. The system of claim 1, wherein the anchor region comprises:
a plurality of physically separate sub-regions in the physical world; or
a first region of the physical world, wherein the first region encloses a second region that is not part of the anchor region.

11. The system of claim 1, wherein the operations further comprise:
defining a non-occludable region enclosed by or adjacent to the anchor region; and
directing the display device not to display the augmented content in the non-occludable region.

12. The system of claim 1, wherein the operations further comprise:
while the viewpoint is directed outside the anchor region:
determining that an event or action occurring while the viewpoint is directed outside the anchor region is associated with displaying the augmented content in the evident manner, and
directing the display device to display the augmented content in the evident manner in response to the determination that the event or action is associated with displaying the augmented content in the evident manner; or
while the viewpoint is directed within the anchor region:
determining that an event or action occurring while the viewpoint is directed within the anchor region is associated with displaying the augmented content in the less evident manner, and
directing the display device to display the augmented content in the less evident manner in response to the determination that the event or action is associated with displaying the augmented content in the less evident manner.

13. The system of claim 12, further comprising a manipulator arm configured to support a tool for use in a procedure performed on a body, wherein:
the event or action associated with displaying the augmented content in the evident manner comprises:
a removal of the tool from the manipulator arm, or
an attachment of the tool to the manipulator arm, or
a manipulation of the tool caused by a user; or
the event or action associated with displaying the augmented content in the less evident manner comprises:
a removal of the tool from the manipulator arm; or
an attachment of the tool to the manipulator arm; or
a manipulation of the tool caused by the user; or
a manipulation of the body or a manipulation of the tool in the body.

14. The system of claim 1, wherein the operations further comprise:
determining that the user moves the viewpoint at a rate greater than a threshold rate; and
directing, in response to the determination that the user moves the viewpoint at the rate greater that the threshold rate, the display device to present the augmented content in the less evident manner.

15. A method comprising:
determining, by a region-based augmentation system, that a viewpoint of a user of a display device is directed within an anchor region of a physical world containing the user, the anchor region having a defined boundary;
directing, by the region-based augmentation system in response to determining that the viewpoint is directed within the anchor region, the display device to present augmented content in an evident manner, wherein the evident manner comprises anchoring the augmented content relative to the viewpoint, such that the augmented content follows the viewpoint as the user moves the viewpoint within the anchor region;
determining, by the region-based augmentation system, that the viewpoint is directed outside of the anchor region by the user, the determining that the viewpoint is directed outside of the anchor region comprising determining that the viewpoint moves across the defined boundary of the anchor region; and
directing, by the region-based augmentation system in response to determining that the viewpoint is directed outside of the anchor region, the display device to present the augmented content in a less evident manner, wherein presenting the augmented content in the less evident manner comprises: presenting the augmented content less visibly than the evident manner or unanchoring the augmented content relative to the viewpoint.

16. The method of claim 15, wherein presenting the augmented content in the less evident manner comprises presenting the augmented content less visibly by:
ceasing the presenting of the augmented content; or
increasing a transparency or a translucency of the augmented content; or
decreasing a size of the augmented content as presented by the display device.

17. The method of claim 15, wherein presenting the augmented content in the less evident manner comprises unanchoring the augmented content relative to the viewpoint by:

ceasing to anchor the augmented content relative to the viewpoint in at least one spatial direction, such that the augmented content does not follow the viewpoint in the at least one spatial direction.

18. The method of claim 15, wherein the method further comprises, subsequent to the determination that the viewpoint is directed outside of the anchor region:
  determining that the viewpoint is again directed within the anchor region; and
  directing, in response to the determination that the viewpoint is again directed within the anchor region, the display device to present the augmented content in the evident manner.

19. The method of claim 15, further comprising:
  defining, by the region-based augmentation system, the anchor region based on a site for a procedure performed in the physical world; or
  referencing, by the region-based augmentation system, the anchor region to an object in the physical world, such that the anchor region moves with the object; or
  defining the anchor region based on an operational stage of the procedure.

20. The method of claim 15, further comprising:
  while the viewpoint is directed outside the anchor region:
    determining, by the region-based augmentation system, that an event or action occurring while the viewpoint is directed outside the anchor region is associated with displaying the augmented content in the evident manner, and
    directing, by the region-based augmentation system, the display device to display the augmented content in the evident manner in response to the determination that the event or action is associated with displaying the augmented content in the evident manner; or
  while the viewpoint is directed within the anchor region:
    determining, by the region-based augmentation system, that an event or action occurring while the viewpoint is directed within the anchor region is associated with displaying the augmented content in the less evident manner, and
    directing, by the region-based augmentation system, the display device to display the augmented content in the less evident manner in response to the determination that the event or action is associated with displaying the augmented content in the less evident manner.

21. A non-transitory computer-readable medium storing instructions that, when executed, direct a processor of a computing device to perform a method comprising:
  determining, by a region-based augmentation system, that a viewpoint of a user of a display device is directed within an anchor region of a physical world containing the user, the anchor region having a defined boundary;
  directing, by the region-based augmentation system in response to determining that the viewpoint is directed within the anchor region, the display device to present augmented content in an evident manner, wherein the evident manner comprises anchoring the augmented content relative to the viewpoint, such that the augmented content follows the viewpoint as the user moves the viewpoint within the anchor region;
  determining, by the region-based augmentation system, that the viewpoint is directed outside of the anchor region by the user, the determining that the viewpoint is directed outside of the anchor region comprising determining that the viewpoint moves across the defined boundary of the anchor region; and
  directing, by the region-based augmentation system in response to determining that the viewpoint is directed outside of the anchor region, the display device to present the augmented content in a less evident manner, wherein presenting the augmented content in the less evident manner comprises: presenting the augmented content less visibly than the evident manner or unanchoring the augmented content relative to the viewpoint.

22. The computer-readable medium of claim 21, wherein presenting the augmented content in the less evident manner comprises unanchoring the augmented content relative to the viewpoint by:
  ceasing to anchor the augmented content relative to the viewpoint in at least one spatial direction, such that the augmented content does not follow the viewpoint in the at least one spatial direction.

23. The computer-readable medium of claim 21, wherein the method further comprises, subsequent to the determination that the viewpoint is directed outside of the anchor region:
  determining that the viewpoint is again directed within the anchor region; and
  directing, in response to the determination that the viewpoint is again directed within the anchor region, the display device to present the augmented content in the evident manner.

24. The computer-readable medium of claim 21, wherein the method further comprises:
  defining, by the region-based augmentation system, the anchor region based on a site for a procedure; or
  referencing, by the region-based augmentation system, the anchor region to an object in the physical world, such that the anchor region moves with the object; or
  defining the anchor region based on an operational stage of the procedure.

25. The computer-readable medium of claim 21, wherein the method further comprises:
  while the viewpoint is directed outside the anchor region:
    determining, by the region-based augmentation system, that an event or action occurring while the viewpoint is directed outside the anchor region is associated with displaying the augmented content in the evident manner, and
    directing, by the region-based augmentation system, the display device to display the augmented content in the evident manner in response to the determination that the event or action is associated with displaying the augmented content in the evident manner; or
  while the viewpoint is directed within the anchor region:
    determining, by the region-based augmentation system, that an event or action occurring while the viewpoint is directed within the anchor region is associated with displaying the augmented content in the less evident manner, and
    directing, by the region-based augmentation system, the display device to display the augmented content in the less evident manner in response to the determination that the event or action is associated with displaying the augmented content in the less evident manner.

* * * * *